United States Patent
Roinestad et al.

(10) Patent No.: US 10,385,007 B2
(45) Date of Patent: Aug. 20, 2019

(54) MONAMINE AND MONOAMINE DERIVATIVES AS INHIBITORS OF LEUKOTRIENE A4 HYDROLASE

(71) Applicant: Celtaxsys, Inc., Atlanta, GA (US)

(72) Inventors: Kurt Roinestad, Atlanta, GA (US); William Guilford, Belmont, CA (US); Tom Kirkland, Atascadero, CA (US); Lopa Bhatt, Roswell, GA (US); Eric Springman, Atlanta, GA (US)

(73) Assignee: Celtaxsys, Inc., Atlanta, GA (US)

( * ) Notice: Subject to any disclaimer, the term of this patent is extended or adjusted under 35 U.S.C. 154(b) by 0 days.

(21) Appl. No.: 15/837,728

(22) Filed: Dec. 11, 2017

(65) Prior Publication Data

US 2018/0162802 A1   Jun. 14, 2018

Related U.S. Application Data

(60) Provisional application No. 62/432,218, filed on Dec. 9, 2016.

(51) Int. Cl.
| | |
|---|---|
| C07C 63/04 | (2006.01) |
| A61K 31/192 | (2006.01) |
| C07C 217/58 | (2006.01) |
| C07C 217/60 | (2006.01) |
| C07D 213/74 | (2006.01) |
| C07C 229/08 | (2006.01) |
| C07C 229/38 | (2006.01) |
| C07C 229/36 | (2006.01) |
| A61P 29/00 | (2006.01) |

(52) U.S. Cl.
CPC ............ *C07C 217/58* (2013.01); *A61P 29/00* (2018.01); *C07C 217/60* (2013.01); *C07C 229/08* (2013.01); *C07C 229/36* (2013.01); *C07C 229/38* (2013.01); *C07D 213/74* (2013.01)

(58) Field of Classification Search
CPC .............................. C07C 63/04; C07C 211/01
USPC .................... 562/473, 441; 564/317; 514/539
See application file for complete search history.

(56) References Cited

U.S. PATENT DOCUMENTS

| | | | |
|---|---|---|---|
| 5,723,492 | A | 3/1998 | Chandrakumar et al. |
| 7,737,145 | B2 | 6/2010 | Arnaiz et al. |
| 9,777,006 | B2 | 10/2017 | Guilford |
| 9,822,106 | B2 | 11/2017 | Guilford et al. |
| 9,856,249 | B2 | 1/2018 | Guilford |
| 2007/0155727 | A1 | 7/2007 | Chen et al. |
| 2008/0033024 | A1 | 2/2008 | Sandanayaka et al. |
| 2010/0210630 | A1 | 8/2010 | Arnaiz et al. |
| 2018/0118735 | A1 | 5/2018 | Guilford et al. |
| 2018/0127424 | A1 | 5/2018 | Guilford |
| 2018/0162854 | A1 | 6/2018 | Guilford |

FOREIGN PATENT DOCUMENTS

| | | | | |
|---|---|---|---|---|
| EP | 0 459 298 A2 | * | 5/1991 | ........... A61K 31/135 |
| EP | 1813623 A1 | | 8/2007 | |
| TW | 201632493 A | | 9/2016 | |
| WO | WO 95/29155 | * | 11/1995 | ........... C07C 275/00 |
| WO | 0059864 A1 | | 10/2000 | |
| WO | 2004043940 A1 | | 5/2004 | |

OTHER PUBLICATIONS

Rubinstein et al.: Antispasmodic ortho-substituted phenoxyalkylamines. J. Med. Chem., vol. 9, pp. 804-809, 1966.*
Rampa, A. et al.: Acetylcholinesterase Inhibitors: SAR and kinetic studies on {N-methyl-N-(3-alkylcarbamoyloxyphenyl)methyl} aminoalkoxyaryl derivatives. J. Med. Chem., vol. 44, pp. 3810-3820, 2001.*
International Search Report and Written Opinion dated Mar. 12, 2018 in corresponding International Application No. PCT/US2017/065593.
Penning et al., "Synthesis of Potent Leukotriene A 4 Hydrolase Inhibitors. Identification of 3-[Methyl] [3-[4-(phenylmethyl)phenoxy]propyl]amino]propanoic Acid", Journal of Medicinal Chemistry, vol. 45, No. 16, Aug. 1, 2002, pp. 3482-3490.
Youngjae Kim et al., "Novel N-biphenyl-2-ylmethyl 2-methoxyphenylpiperazinylalkanamides as 5-HT7R antagonists for the treatment of depression":, Bioorganic & Medicinal Chemistry, vol. 22, No. 17, Sep. 1, 2014, pp. 4587-4596.

(Continued)

*Primary Examiner* — Charanjit Aulakh
(74) *Attorney, Agent, or Firm* — Elmore Patent Law Group, P.C.; Mahreen Chaudhry Hoda; Carolyn S. Elmore

(57) ABSTRACT

This present disclosure is directed to compounds of formula (I):

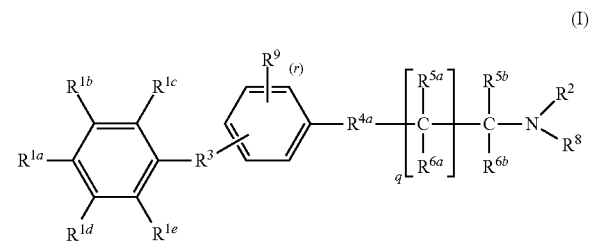

where r, q, $R^{1a}$, $R^{1b}$, $R^{1c}$, $R^{1d}$, $R^{1e}$, $R^2$, $R^3$, $R^{4a}$, $R^{5a}$, $R^{5b}$, $R^{6a}$, $R^{6b}$, $R^8$, and $R^9$ are described herein, as single stereoisomers or as mixtures of stereoisomers, or pharmaceutically acceptable salts, solvates, clathrates, polymorphs, ammonium ions, N-oxides or prodrugs thereof; which are leukotriene $A_4$ hydrolase inhibitors and therefore useful in treating inflammatory disorders. Pharmaceutical compositions including the compounds described herein and methods of preparing the compounds described herein are also provided.

11 Claims, No Drawings

(56) References Cited

OTHER PUBLICATIONS

Kavitha et al.: "Synthesis and screening for acetylcholinesterase inhibitor activity of some novel 2-butyl-1, 3-diaza-spiro [4, 4] non-1-en-4-ones: Derivatives of irbesartan key intermediate", Biorganic & Medicinal Chemistry, vol. 15, No. 23, Oct. 10, 2007, pp. 7391-7398.
Kiefer et al: "Design and synthesis of calindol derivatives as potent and selective calcium sensing receptor agonists", Bioorganic & Medicinal Chemistry, vol. 24, No. 4, Dec. 12, 2015, pp. 554-569.
Ping Wang et al, "Highly Practical and cost-efficient synthesis of telmisartan: an antihypertensive drug", Tetrahedron Elsevier Science Publishers, vol. 68, No. 11, Jan. 18, 2012, pp. 2509-2512.

\* cited by examiner

MONAMINE AND MONOAMINE DERIVATIVES AS INHIBITORS OF LEUKOTRIENE A4 HYDROLASE

CROSS-REFERENCE TO RELATED APPLICATION

The instant patent application claims the benefit of and priority to U.S. Provisional Patent Application Ser. No. 62/432,218 filed on Dec. 9, 2016, the entire content of which is incorporated herein by reference.

TECHNICAL FIELD

This present disclosure describes compounds which include monoamine and monoamine derivatives suitable as leukotriene A4 hydrolase inhibitors and useful in treating inflammatory disorders.

BACKGROUND

Leukotriene $B_4$ ($LTB_4$) is a potent pro-inflammatory activator of inflammatory cells, including neutrophils, monocytes, macrophages, T cells and B cells. Immune cell priming and activation by $LTB_4$ can promote chemotaxis, adhesion, free radical release, degranulation and cytokine release. $LTB_4$ plays a significant role in the amplification of many inflammatory disease states including asthma, inflammatory bowel disease (IBD), chronic obstructive pulmonary disease (COPD), arthritis, psoriasis, and atherosclerosis.

$LTB_4$ levels are elevated in brochoalveolar lavage fluid from patients with scleroderma lung disease. Therefore, a therapeutic agent that inhibits the biosynthesis of LTB4 or the response of cells to $LTB_4$ may be useful for the treatment of these inflammatory conditions.

The biosynthesis of $LTB_4$ from arachidonic acid (AA) involves the action of three enzymes: phospholipase $A_2$ ($PLA_2$), to release AA from the membrane lipids; 5-lipoxygenase (5-LO), to form the unstable epoxide Leukotriene $A_4$ ($LTA_4$); and leukotriene $A_4$ hydrolase ($LTA_4$-h), to form $LTB_4$.

$LTA_4$-h is a monomeric, soluble 69 kD bifunctional zinc-dependent metalloenzyme of the M1 class of metallohydrolases. It catalyzes two reactions: the stereospecific epoxide hydrolase reaction to convert $LTA_4$ to $LTB_4$ and a peptidase cleavage of chromogenic substrates. A reduction of $LTB_4$ production by an inhibitor of $LTA_4$-h activity has therapeutic potential in a wide range of diseases. $LTA_4$-h inhibitors have been shown to be effective anti-inflammatory agents in preclinical studies, thus providing the ability to prevent and/or treat leukotriene-mediated conditions, such as inflammation. $LTA_4$-h inhibitors are disclosed, for example, in U.S. Pat. No. 7,737,145 and U.S. Patent Application Publication No. 2010/0210630A1, the contents of each of which are incorporated by reference herein.

It would be advantageous to develop additional $LTA_4$-h inhibitors.

SUMMARY

The present disclosure describes compounds, as single stereoisomers or as mixtures of stereoisomers, or pharmaceutically acceptable salts, solvates, polymorphs, clathrates, ammonium ions, N-oxides or prodrugs thereof, that inhibit the activity of $LTA_4$-h and are therefore useful as pharmaceutical agents for the treatment of diseases and disorders which are ameliorated by the inhibition of $LTA_4$-h activity.

Accordingly, in one aspect, the disclosure provides compounds of Formula (I):

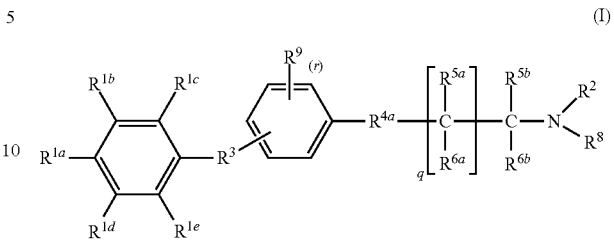

(I)

wherein:
r is 0 to 4; q is 0 to 2;
$R^{1a}$, $R^{1b}$, $R^{1c}$, $R^{1d}$ and $R^{1e}$ are each independently hydrogen, $-R^{13}-OR^{10}$, $-R^{13}-C(=O)OR^{10}$, $-R^{13}-C(=O)R^{10}$, alkyl, halo, haloalkyl, haloalkenyl, haloalkynyl, hydroxyalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, optionally substituted amidinyl, or optionally substituted guanidinyl;

$R^2$ and $R^8$ are each independently hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted arylkyl, optionally substituted heteroaryl, optionally substituted heteroarylalkyl, optionally substituted heterocyclyl, optionally substituted heterocyclylalkyl, $-R^{13}-OR^{10}$, $-R^{13}-O-R^{13}-C(=O)OR^{10}$, $-R^{13}-C(=O)R^{10}$, $-R^{13}-C(=O)OR^{10}$, $-R^{13}-C(=O)-R^{13}-C(=O)OR^{10}$, $-R^{13}-C(=O)-R^{13}-N(R^{10})R^{10}$, $-R^{13}-C(=O)-R^{13}-S(=O)_tN(R^{10})R^{10}$ (where t is 1 or 2), or $-R^{13}-S(=O)_pR^{10}$ (where p is 0, 1 or 2);

or $R^2$ and $R^8$, together with the nitrogen to which they are attached, form an optionally substituted cycloalkyl, optionally substituted cycloalkylalkyl, optionally substituted aryl, optionally substituted heteroaryl, optionally substituted heteroarylalkyl, optionally substituted heterocyclyl, or optionally substituted heterocyclylalkyl;

$R^3$ is a direct bond, $-O-$, $-R^{12}-O-$, $-O-R^{12}-$, $-O-R^{12}-O-$, $-R^{12}-C(=O)R^{12}$, $-R^{12}-O-R^{12}-C(=O)R^{12}$, $-R^{12}-C(=O)-R^{12}-O-R^{12}$, $-R^{12}-O-R^{12}-C(OH)-R^{12}$, $-R^{12}-C(OH)-R^{12}-O-R^{12}$, $-R^{12}-N(R^{10})-R^{12}-$, a straight or branched alkylene chain, a straight or branched alkenylene chain, or a straight or branched alkynylene chain;

$R^{4a}$ is a direct bond, $-O-$, $-R^{12}-O-$, $-O-R^{12}-$, an optionally substituted straight or branched alkylene chain, an optionally substituted straight or branched alkenylene chain, or an optionally substituted straight or branched alkynylene chain;

each $R^{5a}$ and $R^{6a}$ is independently hydrogen, alkyl, halo, haloalkyl, haloalkenyl, haloalkynyl, hydroxyalkyl, optionally substituted cycloalkyl, optionally substituted cycloalkylalkyl, optionally substituted aryl, optionally substituted arylkyl, optionally substituted heteroaryl, optionally substituted heteroarylalkyl, optionally substituted heterocyclyl, or optionally substituted heterocyclylalkyl;

each $R^{5b}$ and $R^{6b}$ is independently hydrogen, alkyl, halo, haloalkyl, haloalkenyl, haloalkynyl, hydroxyalkyl, optionally substituted cycloalkyl, optionally substituted cycloalkylalkyl, optionally substituted aryl, optionally substituted arylkyl, optionally substituted heteroaryl, optionally substituted heteroarylalkyl, optionally substituted heterocyclyl, optionally substituted heterocyclylalkyl, —$R^{13}$—C(=O)—$R^{13}$—O—$R^{10}$, —$R^{13}$—$OR^{13}$—C(=O)$R^{10}$, or —$R^{13}$—$OR^{10}$;

each $R^9$ is independently —O—$R^{10}$, alkyl, hydroxyalkyl, halo, haloalkyl, aryl or aralkyl;

each $R^{10}$ is independently hydrogen, alkyl, halo, haloalkyl, haloalkenyl, haloalkynyl, hydroxyalkyl, optionally substituted cycloalkyl, optionally substituted cycloalkylalkyl, optionally substituted aryl, optionally substituted arylkyl, optionally substituted heteroaryl, optionally substituted heteroarylalkyl, optionally substituted heterocyclyl, or optionally substituted heterocyclylalkyl;

each $R^{12}$ is a direct bond, straight or branched alkylene chain, a straight or branched alkenylene chain, or a straight or branched alkynylene chain; and each $R^{13}$ is independently a direct bond, a straight or branched alkylene chain, a straight or branched alkenylene chain, or a straight or branched alkynylene chain;

as a single stereoisomer or as a mixture of stereoisomers;

or a pharmaceutically acceptable salt, solvate, polymorph, clathrate, ammonium ion, N-oxide or prodrug thereof.

In another aspect, the present disclosure provides pharmaceutical compositions, which composition comprises a therapeutically effective amount of a compound of formula (I) as described above, and a pharmaceutically acceptable excipient.

In another aspect, the present disclosure provides a method of treating a disease or disorder ameliorated by the inhibition of $LTA_4$-h activity in a mammal, which method comprises administering to a mammal in need thereof a therapeutically effective amount of a compound of formula (I) as described above.

DETAILED DESCRIPTION

A detailed description of exemplary embodiments is described in the disclosure that follows.

As used herein the singular forms "a", "an", and "the" include plural referents unless the context clearly dictates otherwise. For example, "a compound" refers to one or more of such compounds, while "the enzyme" includes a particular enzyme as well as other family members and equivalents thereof as known to those skilled in the art.

Furthermore, as used in the specification and appended claims, unless specified to the contrary, the following terms have the meaning indicated:

"Amino" refers to the —$NH_2$ radical.
"Cyano" refers to the —CN radical.
"Hydroxy" refers to the —OH radical.
"Nitro" refers to the —$NO_2$ radical.
"Oxo" refers to the =O radical.
"Alkyl" refers to a straight or branched hydrocarbon chain radical consisting solely of carbon and hydrogen atoms, containing no unsaturation and which is attached to the rest of the molecule by a single bond. In some embodiments, an alkyl group has from one to twelve carbon atoms, one to eight carbon atoms, or one to six carbon atoms. Non-limiting examples of alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like. An optionally substituted alkyl group can be an alkyl group substituted with one or more substituents described in detail below. Non-limiting examples of suitable substituents include: halo, cyano, nitro, oxo, trimethylsilyl, —$OR^{15}$, —OC(=O)—$R^{15}$, —$N(R^{15})_2$, —C(=O)$R^{15}$, —C(=O)$OR^{15}$, —C(=O)$N(R^{15})_2$, —$N(R^{15})$C(=O)$OR^{15}$, —$N(R^{15})$C(=O)$R^{15}$, —$N(R^{15})$S(=O)$_tR^{15}$ (where t is 1 or 2), —S(=O)$_tOR^{15}$ (where t is 1 or 2), —S(=O)$_pR^{15}$ (where p is 0, 1 or 2), and —S(=O)$_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo or alkyl groups), aralkyl, heterocyclyl, heterocyclylalkyl, heteroaryl or heteroarylalkyl, and where each of the above substituents is unsubstituted unless specifically defined otherwise.

"Alkenyl" refers to a straight or branched hydrocarbon chain radical group consisting solely of carbon and hydrogen atoms, containing at least one double bond, having from two to twelve carbon atoms, in embodiments two to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl group may be optionally substituted by one of the following substituents: cyano, nitro, oxo, trimethylsilyl, —$OR^{15}$, —OC(=O)—$R^{15}$, —$N(R^{15})_2$, —C(=O)$R^{15}$, —C(=O)$OR^{15}$, —C(=O)$N(R^{15})_2$, —$N(R^{15})$C(=O)$OR^{15}$, —$N(R^{15})$C(=O)$R^{15}$, —$N(R^{15})$S(=O)$_tR^{15}$ (where t is 1 or 2), —S(=O)$_tOR^{15}$ (where t is 1 or 2), —S(=O)$_pR^{15}$ (where p is 0, 1 or 2), and —S(=O)$_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless specifically defined otherwise.

"Alkynyl" refers to a straight or branched hydrocarbon chain radical group consisting solely of carbon and hydrogen atoms, containing at least one triple bond, optionally containing at least one double bond, having from two to twelve carbon atoms, in embodiments two to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one of the following substituents: cyano, nitro, oxo, trimethylsilyl, —$OR^{15}$, —OC(=O)—$R^{15}$, —$N(R^{15})_2$, —C(=O)$R^{15}$, —C(=O)$OR^{15}$, —C(=O)$N(R^{15})_2$, —$N(R^{15})$C(=O)$OR^{15}$, —$N(R^{15})$C(=O)$R^{15}$, —$N(R^{15})$S(=O)$_tR^{15}$ (where t is 1 or 2), —S(=O)$_tOR^{15}$ (where t is 1 or 2), —S(=O)$_pR^{15}$ (where p is 0, 1 or 2), and —S(=O)$_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless specifically defined otherwise.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one of the following substituents: halo, cyano, nitro, aryl, cycloalkyl, heterocyclyl, heteroaryl, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{15}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following substituents: halo, cyano, nitro, aryl, cycloalkyl, heterocyclyl, heteroaryl, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{15}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following substituents: alkyl, alkenyl, halo, haloalkenyl, cyano, nitro, aryl, cycloalkyl, heterocyclyl, heteroaryl, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{15}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkoxy" refers to a radical of the formula $-OR_a$ where $R_a$ is an alkyl radical as defined above containing one to twelve carbon atoms. The alkyl part of the alkoxy radical may be optionally substituted as defined above for an alkyl radical.

"Alkoxyalkyl" refers to a radical of the formula $-R_a-O-R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"Amidinyl" refers to a radical of the formula $R_x-C(=NR_x)-N(R_x)_2$ wherein each $R_x$ is independently a direct bond, hydrogen, an alkyl, alkenyl, alkynyl, aryl, aralkyl, cycloalkyl, cycloalkylalkyl, heterocyclyl, heteroaryl, heteroarylalkyl as defined herein.

"Guanidinyl" refers to a radical of the formula $(R_z)_2N-C(=NR_z)-N(R_z)_2$ wherein each $R_z$ is independently a direct bond, hydrogen, an alkyl, alkenyl, alkynyl, aryl, aralkyl, cycloalkyl, cycloalkylalkyl, heterocyclyl, heteroaryl, heteroarylalkyl as defined herein.

"Aryl" refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})C(=O)N(R^{15})_2$, $-R^{16}-N(R^{15})S(=O)_tR^{15}$ (where t is 1 or 2), $-R^{16}-S(=O)_tOR^{15}$ (where t is 1 or 2), $-R^{16}-S(=O)_pR^{15}$ (where p is 0, 1 or 2), and $-R^{16}-S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"Aralkyl" refers to a radical of the formula $-R_aR_b$ where $R_a$ is an alkyl radical as defined above and $R_b$ is one or more aryl radicals as defined above, for example, benzyl, diphenylmethyl and the like. The aryl radical(s) may be optionally substituted as described above.

"Aralkenyl" refers to a radical of the formula $-R_cR_b$ where $R_c$ is an alkenyl radical as defined above and $R_b$ is one or more aryl radicals as defined above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula $-R_dR_b$ where $R_d$ is an alkynyl radical as defined above and $R_b$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Aryloxy" refers to a radical of the formula $-OR_b$ where $R_b$ is an aryl group as defined above. The aryl part of the aryloxy radical may be optionally substituted as defined above.

"Aralkyloxy" refers to a radical of the formula —OR$_b$ where R$_b$ is an aralkyl group as defined above. The aralkyl part of the aralkyloxy radical may be optionally substituted as defined above.

"Ammonium ion" refers to a nitrogen within a compound of the present disclosure containing a positive charge due to the additional substitution of the nitrogen with an optionally substituted alkyl group as defined above.

"Clathrates" as used herein refers to substances which fix gases, liquids or compounds as inclusion complexes so that the complex may be handled in solid form and the included constituent (or "guest" molecule) is subsequently released by the action of a solvent or by melting. The term "clathrate" is used interchangeably herein with the phrase "inclusion molecule" or with the phrase "inclusion complex". Clathrates used in the instant disclosure are prepared from cyclodextrins. Cyclodextrins are widely known as having the ability to form clathrates (i.e., inclusion compounds) with a variety of molecules. See, for example, *Inclusion Compounds*, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", *Topics in Current Chemistry* (1988), Vol. 149, pp. 2-44; Weber, E. et al., "Functional Group Assisted Clathrate Formation—Scissor-Like and Roof-Shaped Host Molecules", *Topics in Current Chemistry* (1988), Vol. 149, pp. 45-135; and MacNicol, D. D. et al., "Clathrates and Molecular Inclusion Phenomena", *Chemical Society Reviews* (1978), Vol. 7, No. 1, pp. 65-87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", *Angew. Chem. Int. Ed. Engl.* (1980), Vol. 19, pp. 344-362; U.S. Pat. No. 4,886,788 (Schering A G); U.S. Pat. No. 6,355,627 (Takasago); U.S. Pat. No. 6,288,119 (Ono Pharmaceuticals); U.S. Pat. No. 6,110,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Cyclodextrin" refers to cyclic oligosaccharides consisting of at least six glucopyranose units which are joined together by α(1-4) linkages. The oligosaccharide ring forms a torus with the primary hydroxyl groups of the glucose residues lying on the narrow end of the torus. The secondary glucopyranose hydroxyl groups are located on the wider end. Cyclodextrins have been shown to form inclusion complexes with hydrophobic molecules in aqueous solutions by binding the molecules into their cavities. The formation of such complexes protects the "guest" molecule from loss of evaporation, from attack by oxygen, visible and ultraviolet light and from intra- and intermolecular reactions. Such complexes also serve to "fix" a volatile material until the complex encounters a warm moist environment, at which point the complex will dissolve and dissociate into the guest molecule and the cyclodextrin. For purposes of this disclosure, the six-glucose unit containing cyclodextrin is specified as α-cyclodextrin, while the cyclodextrins with seven and eight glucose residues are designated as β-cyclodextrin and γ-cyclodextrin, respectively. The most common alternative to the cyclodextrin nomenclature is the naming of these compounds as cycloamyloses.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, in embodiments having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantine, norbornane, 7,7-dimethyl-bicyclo[2.2.1]heptanyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —R$^{16}$—OR$^{15}$, —R$^{16}$—OC(=O)—R$^{15}$, —R$^{16}$—N(R$^{15}$)$_2$, —R$^{16}$—C(=O)R$^{15}$, —R$^{16}$—C(=O)OR$^{15}$, —R$^{16}$—C(=O)N(R$^{15}$)$_2$, —R$^{16}$—N(R$^{15}$)C(=O)OR$^{15}$, —R$^{16}$—N(R$^{15}$)C(=O)R$^{15}$, —R$^{16}$—N(R$^{15}$)C(=O)N(R$^{15}$)$_2$, —R$^{16}$—N(R$^{15}$)S(=O)$_t$R$^{15}$ (where t is 1 or 2), —R$^{16}$—S(=O)$_t$OR$^{15}$ (where t is 1 or 2), —R$^{16}$—S(=O)$_p$R$^{15}$ (where p is 0, 1 or 2), and —R$^{16}$—S(=O)$_t$N(R$^{15}$)$_2$ (where t is 1 or 2), where each R$^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each R$^{16}$ is independently a direct bond or a straight or branched alkylene or alkenylene chain.

"Cycloalkylalkyl" refers to a radical of the formula —R$_a$R$_e$ where R$_a$ is an alkyl radical as defined above and R$_e$ is a cycloalkyl radical as defined above. The alkyl radical and the cycloalkyl radical may be optionally substituted as defined above.

"Cycloalkylalkenyl" refers to a radical of the formula —R$_c$R$_e$ where R$_c$ is an alkenyl radical as defined above and R$_e$ is a cycloalkyl radical as defined above. The alkenyl radical and the cycloalkyl radical may be optionally substituted as defined above.

"Cycloalkylalkynyl" refers to a radical of the formula —R$_d$R$_e$ where R$_d$ is an alkynyl radical as defined above and R$_e$ is a cycloalkyl radical as defined above. The alkynyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above that is substituted by one or more halo radicals, as defined above. The alkenyl part of the haloalkyl radical may be optionally substituted as defined above for an alkenyl group.

"Haloalkynyl" refers to an alkynyl radical, as defined above that is substituted by one or more halo radicals, as defined above. The alkynyl part of the haloalkyl radical may be optionally substituted as defined above for an alkynyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azepinyl, 2,5-diazabicyclo[2.2.1]heptan-2-yl, hexahydro-1H-1,4-diazepinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxiranyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—$OC(=O)$—$R^{15}$, —$R^{16}$—$N(R^{15})_2$, —$R^{16}$—$C(=O)R^{15}$—$R^{16}$—$C(=O)OR^{15}$, —$R^{16}$—$C(=O)N(R^{15})_2$, —$R^{16}$—$N(R^{15})C(=O)OR^{15}$, —$R^{16}$—$N(R^{15})C(=O)R^{15}$, —$R^{16}$—$N(R^{15})C(=O)N(R^{15})_2$, —$R^{16}$—$N(R^{15})S(=O)_tR^{15}$ (where t is 1 or 2), —$R^{16}$—$S(=O)_tOR^{15}$ (where t is 1 or 2), —$R^{16}$—$S(=O)_pR^{15}$ (where p is 0, 1 or 2), and —$R^{16}$—$S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula —$R_aR_f$ where $R_a$ is an alkyl radical as defined above and $R_f$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heterocyclylalkenyl" refers to a radical of the formula —$R_cR_f$ where $R_c$ is an alkenyl radical as defined above and $R_f$ is a heterocyclyl radical as defined above, and if the heterocyclyl is a nitrogen-containing heterocyclyl, the heterocyclyl may be attached to the alkenyl radical at the nitrogen atom. The alkenyl part of the heterocyclylalkenyl radical may be optionally substituted as defined above for an alkenyl group. The heterocyclyl part of the heterocyclylalkenyl radical may be optionally substituted as defined above for a heterocyclyl group.

"Heterocyclylalkynyl" refers to a radical of the formula —$R_dR_f$ where $R_d$ is an alkynyl radical as defined above and $R_f$ is a heterocyclyl radical as defined above, and if the heterocyclyl is a nitrogen-containing heterocyclyl, the heterocyclyl may be attached to the alkynyl radical at the nitrogen atom. The alkynyl part of the heterocyclylalkynyl radical may be optionally substituted as defined above for an alkynyl group. The heterocyclyl part of the heterocyclylalkynyl radical may be optionally substituted as defined above for a heterocyclyl group.

"Heteroaryl" refers to a 3- to 18-membered fully or partially aromatic ring radical which consists of one to thirteen carbon atoms and from one to six heteroatoms selected from the group consisting of nitrogen, oxygen and sulfur. For purposes of this disclosure, the heteroaryl radical may be a monocyclic, bicyclic, tricyclic or tetracyclic ring system, which may include fused or bridged ring systems; the nitrogen, carbon or sulfur atoms in the heteroaryl radical may be optionally oxidized; and the nitrogen atom may be optionally quaternized. Examples include, but are not limited to, acridinyl, benzimidazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrazolyl, pyridinyl, pyrazinyl, pyrimidinyl, pyridazinyl, pyrrolyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, oxo, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—$OC(=O)$—$R^{15}$, —$R^{16}$—$N(R^{15})_2$, —$R^{16}$—$C(=O)R^{15}$, —$R^{16}$—$C(=O)OR^{15}$, —$R^{16}$—$C(=O)N(R^{15})_2$, —$R^{16}$—$N(R^{15})C(=O)OR^{15}$, —$R^{16}$—$N(R^{15})C(=O)R^{15}$, —$R^{16}$—$N(R^{15})C(=O)N(R^{15})_2$, —$R^{16}$—$N(R^{15})S(=O)_tR^{15}$ (where t is 1 or 2), —$R^{16}$—$S(=O)_tOR^{15}$ (where t is 1 or 2), —$R^{16}$—$S(=O)_pR^{15}$ (where p is 0, 1 or 2), and —$R^{16}$—$S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —$R_aR_g$ where $R_a$ is an alkyl radical as defined above and $R_g$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula —$R_cR_g$ where $R_c$ is an alkenyl radical as defined above and $R_g$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Heteroarylalkynyl" refers to a radical of the formula —$R_dR_g$ where $R_d$ is an alkynyl radical as defined above and $R_g$ is a heteroaryl radical as defined above. The heteroaryl part of the heteroarylalkynyl radical may be optionally substituted as defined above for a heteroaryl group. The alkynyl part of the heteroarylalkynyl radical may be optionally substituted as defined above for an alkynyl group.

"Hydroxyalkyl" refers to an alkyl radical, as defined above, substituted by one or more hydroxy (—OH) groups. If the hydroxyalkyl radical is attached to a hetero atom (e.g., oxygen or nitrogen), a hydroxy group cannot be attached to a carbon in the alkyl group which is directly attached to the hetero atom.

"Hydroxyiminoalkyl" refers to an alkyl radical, as defined above, substituted by a hydroxyimino (=NOH) group.

"Polymorph" refers to a polymorphic form of the compounds of the present disclosure. Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. In this case, the metastable form, although less stable, may exhibit properties desirable over those of the stable form, such as enhanced solubility or better oral bioavailability.

"Prodrug" is meant to indicate a compound that may be converted under physiological conditions or by solvolysis to a biologically active compound of the present disclosure. Thus, the term "prodrug" refers to a metabolic precursor of a compound of the present disclosure that is pharmaceutically acceptable. A prodrug may be inactive when administered to a subject in need thereof, but is converted in vivo to an active compound of the present disclosure. Prodrugs are typically rapidly transformed in vivo to yield the parent compound of the present disclosure, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers, which release the active compound of the present disclosure in vivo when such prodrug is administered to a mammalian subject. Prodrugs of a compound of the present disclosure may be prepared by modifying functional groups present in the compound of the present disclosure in such a way that the modifications are cleaved, either in routine manipulation or in vivo, to the parent compound of the present disclosure. Prodrugs include compounds of the present disclosure wherein a hydroxy, amino or mercapto group is bonded to any group that, when the prodrug of the compound of the present disclosure is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the present disclosure and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. In embodiments, for purposes of this disclosure, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. In embodiments, inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases are isopropylamine, diethylamine, ethanolamine, trimethylamine, dicyclohexylamine, choline and caffeine.

A "pharmaceutical composition" refers to a formulation of a compound of the present disclosure and a medium generally accepted in the art for the delivery of the biologically active compound to mammals, for example, humans. Such a medium includes all pharmaceutically acceptable carriers, diluents or excipients.

"Solvate" refers to an aggregate that comprises one or more molecules of a compound of the present disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the present disclosure may be true solvates, while in other cases, the compound of the present disclosure may merely retain adventitious water or be a mixture of water plus some adventitious solvent.

"Therapeutically effective amount" refers to that amount of a compound of the present disclosure that, when administered to a mammal, such as a human, is sufficient to effect treatment, as defined below, of a disease or condition of interest in the mammal, such as a human. The amount of a compound of the present disclosure which constitutes a "therapeutically effective amount" will vary depending on, e.g., the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy, but it can be determined routinely by one of ordinary skill in the art having regard to his own knowledge and to this disclosure.

"Treating" or "treatment" as used herein covers the treatment of the disease or condition of interest in a mammal, such as a human, having the disease or condition of interest, and includes:

(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the present disclosure, or their pharmaceutically acceptable salts may contain one or more asymmetric centers and may thus give rise to enantiomers, diastereomers, and other stereoisomeric forms that may be defined, in terms of absolute stereochemistry, as (R) - or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as for example, but not limited to, HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present disclosure includes tautomers of any said compounds.

Pharmaceutical Compositions and Administration

Administration of the compounds of the present disclosure, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the present disclosure in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the present disclosure, or a pharmaceutically acceptable salt thereof, for treatment of a disease or condition of interest in accordance with the teachings of this disclosure.

A pharmaceutical composition of the present disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, particular compositions contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present disclosure, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a particularly useful adjuvant. An injectable pharmaceutical composition is useful when sterile.

A liquid pharmaceutical composition of the present disclosure intended for either parenteral or oral administration should contain an amount of a compound of the present disclosure such that a suitable dosage will be obtained. Typically, this amount is at least 0.01% of a compound of the present disclosure in the composition. When intended for oral administration, this amount may be varied to be between 0.1 and about 70% of the weight of the composition. Some oral pharmaceutical compositions contain between about 4% and about 50% of the compound of the present disclosure. Some pharmaceutical compositions and preparations according to the present disclosure are prepared so that a parenteral dosage unit contains between 0.01 to 10% by weight of the compound prior to dilution.

The pharmaceutical composition of the present disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present disclosure from about 0.1 to about 10% w/v (weight per unit volume).

The pharmaceutical composition of the present disclosure may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the present disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present disclosure in solid or liquid form may include an agent that binds to the compound of the present disclosure and thereby assists in the delivery of the compound. Suitable agents that may act in this capacity include a monoclonal or polyclonal antibody, a protein or a liposome.

The pharmaceutical composition of the present disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present disclosure may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine suitable aerosols.

The pharmaceutical compositions of the present disclosure may be prepared by methodology well known in the pharmaceutical art. For example, a pharmaceutical composition intended to be administered by injection can be prepared by combining a compound of the present disclosure with sterile, distilled water so as to form a solution. A surfactant may be added to facilitate the formation of a homogeneous solution or suspension. Surfactants are compounds that non-covalently interact with the compound of the present disclosure so as to facilitate dissolution or homogeneous suspension of the compound in the aqueous delivery system.

The compounds of the present disclosure, or their pharmaceutically acceptable salts, are administered in a therapeutically effective amount, which will vary depending upon a variety of factors and can be determined routinely by one of ordinary skill in the art. Generally, a therapeutically effective daily dose is (for a 70 kg mammal) from about 0.001 mg/kg (i.e., 0.7 mg) to about 100 mg/kg (i.e., 7.0 gm); in embodiments a therapeutically effective dose is (for a 70 kg mammal) from about 0.01 mg/kg (i.e., 7 mg) to about 50 mg/kg (i.e., 3.5 gm); in some embodiments a therapeutically effective dose is (for a 70 kg mammal) from about 1 mg/kg (i.e., 70 mg) to about 25 mg/kg (i.e., 1.75 gm).

Compounds of the present disclosure, or pharmaceutically acceptable derivatives thereof, may also be administered simultaneously with, prior to, or after administration of one or more other therapeutic agents. Such combination therapy includes administration of a single pharmaceutical dosage formulation which contains a compound of the present disclosure and one or more additional active agents, as well as administration of the compound of the present disclosure and each active agent in its own separate pharmaceutical dosage formulation. For example, a compound of the present disclosure and the other active agent can be administered to the patient together in a single oral dosage composition such as a tablet or capsule, or each agent can be administered in separate oral dosage formulations. Where separate dosage formulations are used, the compounds of the present disclosure and one or more additional active agents can be administered at essentially the same time, i.e., concurrently, or at separately staggered times, i.e., sequentially; combination therapy is understood to include all these regimens.

Examples of classes of agents which may be utilized in combination with the compounds described herein include, without limitation, antimicrobials, analgesics, antipyretics, anesthetics, antiepileptics, antihistamines, anti-asthmatics, anticholesterols, CFTR modulators, CNS drugs, antidepressants, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, enzymes, and combinations thereof.

Utility of the Compounds Described Herein

The compounds of the present disclosure are inhibitors of $LTA_4$-h activity and are therefore useful in treating diseases and disorders which are ameliorated by the inhibition of $LTA_4$-h activity.

Accordingly, the compounds are broadly useful in the treatment of inflammatory conditions and disorders characterized by immune system dysregulation in mammals, particularly humans.

The compounds are particularly useful in the treatment of such conditions where the inflammatory process or immune dysregulation involves the action of neutrophils, macrophages, eosinophils, or T-cells.

Such diseases and their sequelae include pulmonary and respiratory diseases, cardiovascular diseases, gastrointestinal diseases, diseases of the nervous system, metabolic disorders, connective tissue disorders, cancers, dermatologic and mucus membrane conditions, diseases of the eye, and other diseases and conditions.

The compounds are particularly useful in pulmonary and respiratory diseases including, but not limited to, cystic fibrosis, chronic obstructive pulmonary disease, bronchiectasis, interstitial lung disease, pulmonary fibrosis, sarcoidosis, pulmonary hypertension, chronic bronchitis, bronchiolitis, bronchiolitis obliterans, pulmonary manifestations of connective tissue diseases, acute or chronic lung injury, pneumonias, adult respiratory distress syndrome, asthma, allergic inflammation of the respiratory tract (including rhinitis and sinusitis), eosinophilic granuloma, and non-infectious inflammatory disorders of the lung characterized by eosinophil infiltration.

The compounds are also particularly useful in the treatment of cardiovascular diseases including, but not limited to, myocardial infarction or susceptibility to myocardial infarction, transient ischemic attack, stroke or susceptibility of stroke, claudication, arteriosclerosis, peripheral arterial occlusive disease or susceptibility to peripheral arterial occlusive disease, acute coronary syndrome (such as unstable angina, non-ST-elevation myocardial infarction or ST-elevation myocardial infarction), atherosclerosis (including formation of unstable atherosclerotic plaques), pulmonary arterial hypertension, vasculitis, aneurysm, critical leg ischemia, peripheral arterial occlusive disease and Reynaud's syndrome.

The compounds are also particularly useful in the treatment of gastrointestinal disorders including, but not limited to, irritable bowel syndrome, inflammatory bowel disease, Crohn's disease, ulcerative colitis, pouchitis, fistulas, gastrointestinal ulcers, Barrett's esophagus, and eosinophilic esophagitis.

The compounds are also useful for treating metabolic diseases and their sequelae including, but not limited to, development and consequences of insulin resistance, insulin and non-insulin dependent forms of diabetes mellitus, diabetic ulcers, fatty liver disease, non-alcoholic steatohepatitis, liver fibrosis, sarcopenia, treatment and/or prevention of gout flares, treatment of gouty arthritis.

The compounds are also particularly useful in the treatment of nervous system diseases including, but not limited to, multiple sclerosis, relapsing-remitting multiple sclerosis, chronic progressive multiple sclerosis, and secondary progressive multiple sclerosis, neuropathic pain, amyotrophic lateral sclerosis, delayed neurodegeneration in stroke, Alzheimer's disease, Parkinson's disease, encephalitis, migraine, and HIV dementia.

The compounds are also particularly useful in the treatment of connective tissues diseases and their sequelae including, but not limited to, rheumatoid arthritis, osteoarthritis, osteoporosis, systemic lupus erythematosus, Sjogren-Larsson Syndrome, scleroderma, and pulmonary hypertension resulting from connective tissue diseases.

The compounds are also particularly useful in the prevention and treatment of cancers including, but not limited to, leukemias, lymphomas, cutaneous T-cell lymphoma, mycosis fungoides, Sezary Syndrome, prostate cancer, breast cancer, lung cancers, malignant melanoma, squamous cell carcinoma, basal cell carcinoma, renal carcinoma, head and neck tumors, colorectal cancer, esophageal cancers, and hepatocellular carcinoma.

The compounds are also particularly useful in the treatment of dermatologic and mucus membrane conditions and diseases including, but not limited to, various forms of neutrophilic dermatoses, bullous dermatoses, dermatitis, and acneiform diseases. Neutrophilic dermatoses include, but are not limited to, hidradenitis suppurativa, neutrophilic eccrine hidradenitis, pyoderma gangrenosum, Sweet Syndrome, Behcet disease, and palmoplantar pustulosis. Bullous dermatoses include, but are not limited to, bullous pemphigoid, epidermolysis bullosa acquisita, pemphigus vulgaris, mucus membrane pemphigoid, and dermatitis herpetiformis. Dermatitis conditions include, but are not limited to, atopic dermatitis, contact dermatitis, and urticaria.

Acneiform conditions include, but are not limited to, acne vulgaris, rosacea, and folliculitis.

The compounds are also useful for the treatment of diseases of the eye including, but not limited to, uveitis, macular degeneration, and glaucoma.

The compounds are also particularly useful in the treatment of other disease including, but not limited to, lymphedema, periodontal disease, gingivitis, benign prostatic hyperplasia, pancreatitis, and acute and chronic transplant rejection.

A topical formulation of the compounds is particularly useful for the treatment of dermatologic and mucus membrane diseases, diseases of the eye, and pulmonary and respiratory diseases.

The compounds are also useful in inhibiting the synthesis of leukotriene $B_4$ in both in vitro and in vivo assays.

Testing of the Compounds Described Herein

Testing of the compounds described herein including the following three (3) assays: a $LTA_4$ hydrolase homogeneous time resolved fluorescence assay; a peptidase assay; and, a whole blood assay.

$LTA_4$ Hydrolase Homogeneous Time Resolved Fluorescence Assay

Compounds of the invention were tested in the $LTA_4$ hydrolase homogeneous time resolved fluorescence (HTRF) assay to determine their ability to inhibit the hydrolysis of $LTA_4$ to $LTB_4$. The assay analyzes the amount of $LTB_4$ produced.

$LTA_4$ HTRF assay is a two-step assay involving enzymatic conversion of $LTA_4$ to $LTB_4$, and subsequent quantification of $LTB_4$, product with HTRF assay.

The enzymatic conversion of $LTA_4$ to $LTB_4$ was performed in 384-well plates at ambient temperature in a reaction mixture containing 50 mM HEPES (pH 7.5), 0.5% BSA (fatty acid free), 18 nM recombinant human $LTA_4$ hydrolase, 150 nM $LTA_4$, 1% DMSO in the absence or presence of a compound of the invention. Reaction was stopped after 10 minutes incubation by diluting the incubation mixture 10-fold in 50 mM phosphate, 0.1% casein buffer (pH 7.0).

$LTB_4$ formed was quantified with the HTRF assay in which free $LTB_4$ competes with $LTB_4$-XL665 conjugate (acceptor) for anti-$LTB_4$ monoclonal antibody labeled with Europium cryptate (donor), thereby inhibiting the fluorescence energy transfer.

The $LTB_4$ HTRF 384-well assay was carried out by incubating $LTB_4$ samples or standards with $LTB_4$-XL665 conjugate (7.5 ng/well) and anti-$LTB_4$ monoclonal antibody-Europium cryptate conjugate (0.5 ng/well) in 50 mM phosphate, 0.4 M KF and 0.1% casein, buffer (pH 7.0) for two hours at ambient temperature. Plates were read in a RubyStar plate reader (BmG Labtechnologies Inc., NC) simultaneously at 620 nm and 665 nm to obtain signal ratios of 665 nm/620 nm. Results of energy transfer were expressed as delta F (%) which equaled [(signal ratio of sample-signal ratio of negative control)/(signal ratio of negative control)]×100%. Negative controls were control samples without $LTB_4$ or $LTB_4$-XL665.

Sample $LTB_4$ concentrations were calculated from the $LTB_4$ standard curve using the 4-parameter fit equation. For determination $IC_{50}$ values for a particular compound of the invention, eight serially diluted compound concentrations (at 1:3.16 dilution) were used in this assay. Controls without a compound of the invention or with a reference compound were run parallel in the same assay plate.

Compounds of the invention, when tested in this assay, demonstrated the ability to inhibit $LTA_4$ hydrolase activity at $IC_{50}$ values of less than 100 μM, in some embodiments less than 1 μM, in some embodiments less than 300 nM, in some embodiments less than 100 nM, in some embodiments less than 75 nM, in some embodiments less than 50 nM, in some embodiments less than 25 nM, in some embodiments less than 10 nM, in some embodiments less than 5 nM.

In embodiments, the compounds of the invention, when tested in this assay, demonstrated the ability to inhibit $LTA_4$ hydrolase activity at $IC_{50}$ values from 0.01 nM to 10 μM, in embodiments from 0.05 nM to 300 nM, in embodiments from 0.1 nM to 250 nM, in embodiments from 0.5 nM to 200 nM, in some embodiments from 0.5 nM to 75 nM, in embodiments from 1 nM to 250 nM, in embodiments from 5 nM to 200 nM, in some embodiments from 5 nM to 150 nM, in some embodiments from 5 nM to 125 nM.

Peptidase Assay

Inhibition of peptidase activity was measured for the compounds of the invention by using methods similar to those described in Kull, F. et al., *The Journal of Biological Chemistry* 1999, 274 (49): 34683-34690. In particular, the peptidase activity of the compounds was measured by inhibition of the hydrolysis of L-alanine-p-nitroanilide to L-alanine and highly colored nitro-aniline as set forth below in the following reaction

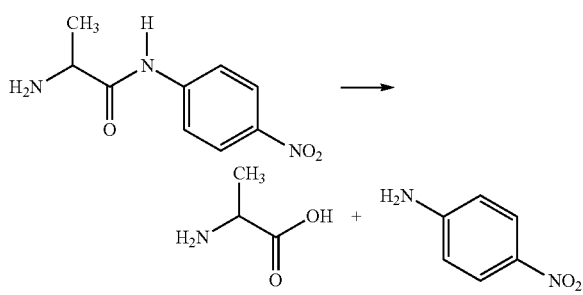

In brief, the enzyme (29 nM) was incubated with L-alanine-p-nitroanilide (1 mM) in 50 mM HEPES (pH 7.5), 100 mM KCL, 1% DMSO in the absence or presence of a compound of the invention for 1 hour at ambient temperature. Reaction was terminated by addition of acetic acid (1%). Formation of colored nitro-aniline was measured by the increase in absorbance at 405 nm in a Victor 2 plate reader (Wallac). Spontaneous hydrolysis of the substrate was corrected for by subtracting the absorbance of control incubations without enzyme.

In embodiments, the compounds of the invention, when tested in this assay, demonstrated the ability to inhibit peptidase activity at $IC_{50}$ values of less than 100 µM, in some embodiments less than 1 µM, in some embodiments less than 100 nM, in some embodiments less than 75 nM, in some embodiments less than 50 nM, in some embodiments less than 25 nM, in some embodiments less than 10 nM, in some embodiments less than 5 nM.

In embodiments, the compounds of the invention, when tested in this assay, demonstrated the ability to inhibit peptidase activity at IC50 values from 0.01 nM to 10 µM, in some embodiments from 0.1 nM to 200 nM, in some embodiments from 0.1 nM to 100 nM, in some embodiments from 0.5 nM to 180 nM, in some embodiments from 0.5 nM to 75 nM, from some embodiments from 1 nM to 50 nM, in some embodiments from 1 nM to 200 nM, in some embodiments from 20 nM to 180 nM, in some embodiments from 5 nM to 25 nM, in some embodiments from 5 nM to 35 nM, in some embodiments from 20 nM to 35 nM.

Compounds of the invention, when tested in both $LTA_4$ hydrolase and/or peptidase assays described herein, demonstrated the ability to inhibit $LTA_4$ hydrolase activity and/or peptidase activity at $IC_{50}$ values of less than 100 µM, in some embodiments less than 1 nM, in some embodiments less than 200 nM, in some embodiments less than 100 nM, in some embodiments less than 75 nM, in some embodiments less than 50 nM, in some embodiments less than 25 nM, in some embodiments less than 10 nM.

Compounds of the invention, when tested in both the $LTA_4$ hydrolase and/or peptidase assays described herein, demonstrated the ability to inhibit $LTA_4$ hydrolase activity and/or peptidase activity at $IC_{50}$ values from 0.01 nM to 10 µM, in embodiments from 0.1 nM to 100 nM, in some embodiments from 0.5 nM to 75 nM, in some embodiments from 1 nM to 50 nM, in some embodiments from 1 nM to 25 nM, in some embodiments from 1 nM to 10 nM, in some embodiments from 5 nM to 300 nM, in some embodiments from 6 nM to 180 nM Whole Blood Assay Compounds of the invention were tested for their ability as inhibitors of $LTA_4$ hydrolase in a whole blood assay using human, mouse, rat or dog whole blood in a manner similar to that described in Penning, T. D. et al., *J. Med. Chem.* (2000), 43(4): 721-735. In this assay, compounds were tested for their ability to inhibit $LTB_4$ release upon stimulation with calcium ionophore. The $LTB_4$ levels in supernatants were measured by ELISA.

Compounds of the invention inhibited the release or production of $LTB_4$ upon addition of calcium ionophore in a dose-dependent manner from whole blood in all species tested.

In embodiments, the compounds of the invention, when tested in this assay, demonstrated the ability to inhibit production of $LTB_4$ in whole blood at $IC_{50}$ values of less than 100 µM, in some embodiments less than 10 µM, in some embodiments less than 1 uM, in some embodiments less than 500 nM, in some embodiments less than 250 nM, in some embodiments less than 125 nM, in some embodiments less than 100 nM, in some embodiments less than 75 nM.

In embodiments, the compounds of the invention, when tested in this assay, demonstrated the ability to inhibit production of $LTB_4$ in whole blood at $IC_{50}$ values from 0.01 nM to 10 µM, in some embodiments from 0.1 nM to 1 uM, in some embodiments from 0.5 nM to 500 nM, from some embodiments from 1 nM to 250 nM, in some embodiments from 5 nM to 125 nM, in some embodiments from 50 nM to 100 nM.

Compounds of the invention, when tested in all three assays described herein, i.e., the $LTA_4$ hydrolase assay, the peptidase assay, and/or the whole blood assay, demonstrated the ability to inhibit $LTA_4$ hydrolase activity, peptidase activity, and/or the production of $LTB_4$ in whole blood at $IC_{50}$ values of less than 100 µM, in some embodiments less than 1 µM, in some embodiments less than 100 nM, in some embodiments less than 75 nM.

Compounds of the invention, when tested in all three assays described herein, i.e., the $LTA_4$ hydrolase assay, the peptidase assay, and/or the whole blood assay, demonstrated the ability to inhibit $LTA_4$ hydrolase activity, peptidase activity, and/or the production of $LTB_4$ in whole blood at $IC_{50}$ values of from 1 nM to 1000 nM, in some embodiments from 5 nM to 500 nM, in some embodiments from 10 nM to 250 nM, 0.01 nM to 10 µM, in embodiments from 0.1 nM to 100 nM, in some embodiments from 0.5 nM to 75 nM, in some embodiments from 1 nM to 100 nM, in some embodiments from 2 nM to 75 nM.

Exemplary Embodiments

The present disclosure describes compounds of Formula (I), as single stereoisomers or as mixtures of stereoisomers, and the pharmaceutically acceptable salts, solvates, polymorphs, clathrates, ammonium ions, N-oxides or prodrugs thereof, as set forth above in the Summary.

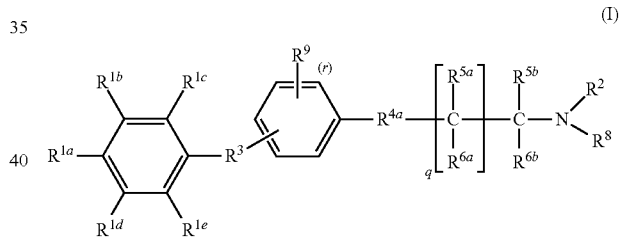

(I)

wherein r, q, $R^{1a}$, $R^{1b}$, $R^{1c}$, $R^{1d}$, $R^{1e}$, $R^2$, $R^3$, $R^{4a}$, $R^{5a}$, $R^{5b}$, $R^{6a}$, $R^{6b}$, $R^8$, and $R^9$ are as described above in the Summary.

In embodiments, the compounds of Formula (I) are those wherein $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; and r, q, $R^2$, $R^3$, $R^{4a}$, $R^{5a}$, $R^{5b}$, $R^{6a}$, $R^{6b}$, $R^8$, and $R^9$, are as described above in the Summary.

In embodiments, the compounds of Formula (I) are those wherein $R^3$ is a direct bond, —O—, —$R^{12}$—O—, —O—$R^{12}$—, or a straight or branched alkylene chain; and r, q, $R^{1a}$, $R^{1b}$, $R^{1c}$, $R^{1d}$, $R^{1e}$, $R^2$, $R^{4a}$, $R^{5a}$, $R^{5b}$, $R^{6a}$, $R^{6b}$, $R^8$, and $R^9$, are as described above in the Summary.

In embodiments, the compounds of Formula (I) are those wherein $R^{4a}$ is a direct bond or —O—; $R^{5a}$ and $R^{6a}$ are each independently hydrogen or halo; and r, q, $R^{1a}$, $R^{1b}$, $R^{1c}$, $R^{1d}$, $R^{1e}$, $R^2$, $R^{5b}$, $R^{6b}$, $R^8$, and $R^9$, are as described above in the Summary.

In embodiments, the compounds of Formula (I) are those wherein q is 1 to 2; $R^{5b}$ and $R^{6b}$ are each independently hydrogen, —$R^{13}$—O$R^{13}$—C(=O)$R^{10}$, or —$R^{13}$—O$R^{10}$ and r, $R^{1a}$, $R^{1b}$, $R^{1c}$, $R^{1d}$, $R^{1e}$, $R^2$, $R^3$, $R^{4a}$, $R^{5a}$, $R^{6a}$, $R^8$, and $R^9$, are as described above in the Summary.

In embodiments, the compounds of Formula (I) are those wherein $R^2$ and $R^8$ are each independently hydrogen, optionally substituted aryl, optionally substituted heteroarylalkyl, optionally substituted heterocyclyl, optionally substituted heterocyclylalkyl, —$R^{13}$—O—$R^{13}$—C(=O)O$R^{10}$; and r, q, $R^{1a}$, $R^{1b}$, $R^{1c}$, $R^{1d}$, $R^{1e}$, $R^{4a}$, $R^{5a}$, $R^{5b}$, $R^{6a}$, $R^{6b}$, and $R^9$, are as described above in the Summary.

In embodiments, the compounds of Formula (I) are those wherein $R^2$ and $R^8$ are each independently an aralkyl or a heteroaryl, optionally substituted with one or more substituents selected from the group consisting of halo, —$R^{13}$—O$R^{10}$, —$R^{13}$—O$R^{10}$—C(=O)$R^{10}$, —$R^{13}$—C(=O)$R^{10}$, —$R^{13}$—C(=O)O$R^{10}$, —$R^{13}$—C(=O)—$R^{13}$—N($R^{10}$)$R^{10}$, —$R^{13}$—C(=O)N($R^{10}$)—$R^{13}$—N($R^{10}$)$R^{10}$, —$R^{13}$—S(=O)$_t$N($R^{10}$)$R^{10}$ (where t is 1 or 2), —$R^{13}$—N($R^{10}$)$R^{10}$, —$R^{13}$—N($R^{10}$)C(=O)$R^{10}$, —$R^{13}$—N($R^{10}$)C(=O)—$R^{13}$—N($R^{10}$)$R^{10}$, —$R^{13}$—N($R^{10}$)—$R^{13}$—C(=O)O$R^{10}$, —$R^{13}$—N($R^{10}$)C(=O)—$R^{13}$—S(=O)$_t$N($R^{10}$)$R^{10}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{13}$—N($R^{10}$)$R^{10}$, —$R^{13}$—N($R^{10}$)S(=O)$_t$N($R^{10}$)$R^{10}$ (where t is 1 or 2), and —$R^{13}$—O—$R^{13}$—C(=O)O$R^{10}$; and r, q, $R^{1a}$, $R^{1b}$, $R^{1c}$, $R^{1d}$, $R^{1e}$, $R^{4a}$, $R^{5a}$, $R^{5b}$, $R^{6a}$, $R^{6b}$, and $R^9$, are as described above in the Summary.

In embodiments, the compounds of Formula (I) are those wherein: $R^2$ and $R^8$, together with the nitrogen to which they are attached, form an optionally substituted optionally substituted heteroaryl, or optionally substituted heterocyclyl; and r, q, $R^{1a}$, $R^{1b}$, $R^{1c}$, $R^{1d}$, $R^{1e}$, $R^{4a}$, $R^{5a}$, $R^{5b}$, $R^{6a}$, $R^{6b}$, and $R^9$, are as described above in the Summary.

In some embodiments, $R^2$ and $R^8$, together with the nitrogen to which they are attached, form an optionally substituted heterocyclyl or an optionally substituted heteroaryl.

In some embodiments, $R^2$ and $R^8$, together with the nitrogen to which they are attached, form an optionally substituted N-heterocyclyl. In embodiments, the N-heterocyclyl is monocyclic. In embodiments, the N-heterocyclyl is bicyclic. In embodiments, the N-heterocyclyl is a 3- to 7-membered ring. In embodiments, the N-heterocyclyl is a 5-membered ring.

In some embodiments, $R^2$ and $R^8$, together with the nitrogen to which they are attached, form an optionally substituted heteroaryl. In embodiments, the heteroaryl is monocyclic. In embodiments, the heteroaryl is bicyclic. In embodiments, the heteroaryl is a 3- to 10-membered ring. In embodiments, the heteroaryl is a 9-membered ring. In embodiments, the heteroaryl is a 9-membered fused ring including 3 nitrogen. In embodiments, the heteroaryl contains multiple nitrogen. In embodiments, the heteroaryl is a pyridinyl.

In embodiments, $R^2$ and $R^8$, together with the nitrogen to which they are attached, form an optionally substituted pyridinyl.

In embodiments, $R^2$ and $R^8$, together with the nitrogen to which they are attached, form a pyridinyl substituted with —$R^{13}$—N($R^{10}$)($R^{10}$).

In embodiments, $R^2$ and $R^8$, together with the nitrogen to which they are attached, form a pyridinyl substituted with alkyl-NH$_2$. In embodiments, the pyridinyl is substituted at the ortho position.

In embodiments, the compounds of Formula (I) are those wherein r is 0; q is 0 to 2; $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —$R^{12}$—O—, —O—$R^{12}$—, or a straight or branched alkylene chain; $R^{4a}$ is a direct bond, or —O—; $R^{5a}$ and $R^{6a}$ are each independently hydrogen; $R^{5b}$ and $R^{6b}$ are each independently hydrogen, —$R^{13}$—O$R^{10}$—C(=O)$R^{10}$, or —$R^{13}$—O$R^{10}$; $R^2$ and $R^8$ are each independently hydrogen, optionally substituted aryl, optionally substituted heteroarylalkyl, optionally substituted heterocyclyl, optionally substituted heterocyclylalkyl, —$R^{13}$—O—$R^{13}$—C(=O)O$R^{10}$; and each $R^{10}$ is independently a hydrogen, alkyl, haloalkyl and each $R^{13}$ is independently a direct bond or a straight or branched alkylene chain.

In embodiments, the compounds of Formula (I) are those wherein r is 0; q is 0 to 2; $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —$R^{12}$—O—, —O—$R^{12}$—, or a straight or branched alkylene chain; $R^{4a}$ is a direct bond, or —O—; $R^{5a}$ and $R^{6a}$ are each independently hydrogen; $R^{5b}$ and $R^{6b}$ are each independently hydrogen, —$R^{13}$—O$R^{11}$—C(=O)$R^{10}$, or —$R^{13}$—O$R^{10}$; $R^2$ and $R^8$ are each independently an aralkyl or a heteroaryl, optionally substituted with one or more substituents selected from the group consisting of halo, —$R^{13}$—O$R^{10}$—C(=O)$R^{10}$, —$R^{13}$—C(=O)O$R^{10}$, —$R^{13}$—N($R^{10}$)$R^{10}$; and each $R^{10}$ is independently a hydrogen, alkyl, haloalkyl and each $R^{13}$ is independently a direct bond or a straight or branched alkylene chain.

In embodiments, the compounds of Formula (I) are those wherein r is 0; q is 0 to 2; $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —$R^{12}$—O—, —O—$R^{12}$—, or a straight or branched alkylene chain; $R^{4a}$ is a direct bond, or —O—; $R^{5a}$ and $R^{6a}$ are each independently hydrogen; $R^{5b}$ and $R^{6b}$ are each independently hydrogen, —$R^{13}$—O$R^{10}$—C(=O)$R^{10}$, or —$R^{13}$—O$R^{10}$; $R^2$ and $R^8$, together with the nitrogen to which they are attached, form an optionally substituted optionally substituted heteroaryl, or optionally substituted heterocyclyl; each $R^{10}$ is independently a hydrogen, alkyl, haloalkyl and each $R^{13}$ is independently a direct bond or a straight or branched alkylene chain.

In embodiments, the compounds of Formula (I) are those wherein r is 0; q is 0 to 2; $R^{1a}R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —$R^{12}$—O—, —O—$R^{12}$—, or a straight or branched alkylene chain; $R^{4a}$ is a direct bond, or —O—; $R^{5a}$ and $R^{6a}$ are each independently hydrogen; $R^{5b}$ and $R^{6b}$ are each independently hydrogen, —$R^{13}$—O$R^{101}$—C(=O)$R^{10}$, or —$R^{13}$—O$R^{10}$; $R^2$ and $R^8$, together with the nitrogen to which they are attached, form an optionally substituted optionally substituted heteroaryl, or optionally substituted heterocyclyl; each $R^{10}$ is independently a hydrogen, alkyl, haloalkyl and each $R^{13}$ is independently a direct bond or a straight or branched alkylene chain.

The present disclosure describes compounds of Formula (Ia), as single stereoisomers or as mixtures of stereoisomers, and the pharmaceutically acceptable salts, solvates, polymorphs, clathrates, ammonium ions, N-oxides or prodrugs thereof, as set forth above in the Summary.

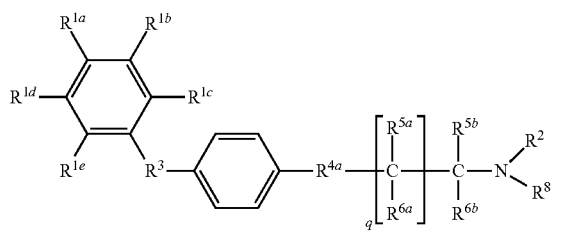

(Ia)

wherein r, q, $R^{1a}$, $R^{1b}$, $R^{1c}$, $R^{1d}$, $R^{1e}$, $R^2$, $R^3$, $R^{4a}$, $R^{5a}$, $R^{5b}$, $R^{6a}$, $R^{6b}$, $R^8$, and $R^9$ are as described above in the Summary.

In embodiments, the compounds of Formula (Ia) are those wherein $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; and r, q, $R^2$, $R^3$, $R^{4a}$, $R^{5a}$, $R^{5b}$, $R^{6a}$, $R^{6b}$, $R^8$, and $R^9$, are as described above in the Summary.

In embodiments, the compounds of Formula (Ia) are those wherein $R^3$ is a direct bond, —O—, —$R^{12}$—O—, —O—$R^{12}$—, or a straight or branched alkylene chain; and r, q, $R^{1a}$, $R^{1b}$, $R^{1c}$, $R^{1d}$, $R^{1e}$, $R^2$, $R^{4a}$, $R^{5a}$, $R^{5b}$, $R^{6a}$, $R^{6b}$, $R^8$, and $R^9$, are as described above in the Summary.

In embodiments, the compounds of Formula (Ia) are those wherein $R^{4a}$ is a direct bond or —O—; $R^{5a}$ and $R^{6a}$ are each independently hydrogen or halo; and r, q, $R^{1a}$, $R^{1b}$, $R^{1c}$, $R^{1d}$, $R^{1e}$, $R^2$, $R^{5b}$, $R^{6b}$, $R^8$, and $R^9$, are as described above in the Summary.

In embodiments, the compounds of Formula (Ia) are those wherein q is 1 to 2; $R^{5b}$ and $R^{6b}$ are each independently hydrogen, —$R^{13}$—C(=O)—$R^{13}$—O—$R^{10}$, —$R^{13}$—O$R^{13}$—C(=O)$R^{10}$, or —$R^{13}$—O$R^{10}$ and r, $R^2$, $R^3$, $R^{4a}$, $R^{5a}$, $R^{6a}$, $R^8$, and $R^9$, are as described above in the Summary.

In embodiments, the compounds of Formula (Ia) are those wherein $R^2$ and $R^8$ are each independently hydrogen, optionally substituted aryl, optionally substituted heteroarylalkyl, optionally substituted heterocyclyl, optionally substituted heterocyclylalkyl, —$R^{13}$—O—$R^{13}$—C(=O)O$R^{10}$; and r, q, $R^{1a}$, $R^{1b}$, $R^{1c}$, $R^{1d}$, $R^{1e}$, $R^{4a}$, $R^{5a}$, $R^{5b}$, $R^{6a}$, $R^{6b}$, and $R^9$, are as described above in the Summary.

In embodiments, the compounds of Formula (Ia) are those wherein $R^2$ and $R^8$ are each independently an aralkyl or a heteroaryl, optionally substituted with one or more substituents selected from the group consisting of halo, —$R^{13}$—O$R^{10}$, —$R^{13}$—O$R^{10}$—C(=O)$R^{10}$, —$R^{13}$—C(=O)$R^{10}$, —$R^{13}$—C(=O)O$R^{10}$, —$R^{13}$—C(=O)—$R^{13}$—N($R^{10}$)$R^{10}$, —$R^{13}$—C(=O)N($R^{10}$) $R^{13}$—N($R^{10}$)$R^{10}$, —$R^{13}$—S(=O)$_t$N($R^{10}$)$R^{10}$ (where t is 1 or 2), —$R^{13}$—N($R^{10}$)$R^{10}$, —$R^{13}$—N($R^{10}$)C(=O)$R^{10}$, —$R^{13}$—N($R^{10}$)C(=O)—$R^{13}$—N($R^{10}$)$R^{10}$, —$R^{13}$—N($R^{10}$)—$R^{13}$—C(=O)O$R^{10}$, —$R^{13}$—N($R^{10}$)C(=O)—$R^{13}$—S(=O)$_t$N($R^{10}$)$R^{10}$ (where t is 1 or 2), —$R^{13}$—N($R^{10}$)C(=O)—$R^{13}$—N($R^{10}$)C(=O) $R^{10}$, —$R^{13}$—N($R^{10}$)C(=O)—$R^{13}$—N($R^{10}$)—$R^{13}$—N($R^{10}$) $R^{10}$, —$R^{13}$—N($R^{10}$)S(=O)$_t$N($R^{10}$)$R^{10}$ (where t is 1 or 2), and —$R^{13}$—O—$R^{13}$—C(=O)O$R^{10}$; and r, q, $R^{1a}$, $R^{1b}$, $R^{1c}$, $R^{1d}$, $R^{1e}$, $R^{4a}$, $R^{5a}$, $R^{5b}$, $R^{6a}$, $R^{6b}$, and $R^9$, are as described above in the Summary.

In embodiments, the compounds of Formula (Ia) are those wherein: $R^2$ and $R^8$, together with the nitrogen to which they are attached, form an optionally substituted optionally substituted heteroaryl, or optionally substituted heterocyclyl; and r, q, $R^{1a}$, $R^{1b}$, $R^{1c}$, $R^{1d}$, $R^{1e}$, $R^{4a}$, $R^{5a}$, $R^{5b}$, $R^{6a}$, $R^{6b}$, and $R^9$, are as described above in the Summary.

In some embodiments, $R^2$ and $R^8$, together with the nitrogen to which they are attached, form an optionally substituted heterocyclyl or an optionally substituted heteroaryl.

In some embodiments, $R^2$ and $R^8$, together with the nitrogen to which they are attached, form an optionally substituted N-heterocyclyl. In embodiments, the N-heterocyclyl is monocyclic. In embodiments, the N-heterocyclyl is bicyclic. In embodiments, the N-heterocyclyl is a 3- to 7-membered ring. In embodiments, the N-heterocyclyl is a 5-membered ring.

In some embodiments, $R^2$ and $R^8$, together with the nitrogen to which they are attached, form an optionally substituted heteroaryl. In embodiments, the heteroaryl is monocyclic. In embodiments, the heteroaryl is bicyclic. In embodiments, the heteroaryl is a 3- to 10-membered ring. In embodiments, the heteroaryl is a 9-membered ring. In embodiments, the heteroaryl contains multiple nitrogen. In embodiments, the heteroaryl is a pyridinyl.

In embodiments, the compounds of Formula (Ia) are those wherein r is 0; q is 0 to 2; $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —$R^{12}$—O—, —O—$R^{12}$—, or a straight or branched alkylene chain; $R^{4a}$ is a direct bond, or —O—; $R^{5a}$ and $R^{6a}$ are each independently hydrogen; $R^{5b}$ and $R^{6b}$ are each independently hydrogen, —$R^{13}$—O$R^{10}$— C(=O)$R^{10}$, or —$R^{13}$—O$R^{10}$; $R^2$ and $R^8$ are each independently hydrogen, optionally substituted aryl, optionally substituted heteroarylalkyl, optionally substituted heterocyclyl, optionally substituted heterocyclylalkyl, —$R^{13}$—O—$R^{13}$— C(=O)O$R^{10}$; and each $R^{10}$ is independently a hydrogen, alkyl, haloalkyl and each $R^{13}$ is independently a direct bond or a straight or branched alkylene chain.

In embodiments, the compounds of Formula (Ia) are those wherein r is 0; q is 0 to 2; $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —$R^{12}$—O—, —O—$R^{12}$—, or a straight or branched alkylene chain; $R^{4a}$ is a direct bond, or —O—; $R^{5a}$ and $R^{6a}$ are each independently hydrogen; $R^{5b}$ and $R^{6b}$ are each independently hydrogen, —$R^{13}$—O$R^{11}$— C(=O)$R^{10}$, or —$R^{13}$—O$R^{10}$; $R^2$ and $R^8$ are each independently an aralkyl or a heteroaryl, optionally substituted with one or more substituents selected from the group consisting of halo, —$R^{13}$—O$R^{10}$—C(=O)$R^{10}$, —$R^{13}$—C(=O)O$R^{10}$, —$R^{13}$—N($R^{10}$)$R^{10}$; and each $R^{10}$ is independently a hydrogen, alkyl, haloalkyl and each $R^{13}$ is independently a direct bond or a straight or branched alkylene chain.

In embodiments, the compounds of Formula (Ia) are those wherein r is 0; q is 0 to 2; $R^{1a}$, $R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —$R^{12}$—O—, —O—$R^{12}$—, or a straight or branched alkylene chain; $R^{4a}$ is a direct bond, or —O—; $R^{5a}$ and $R^{6a}$ are each independently hydrogen; $R^{5b}$ and $R^{6b}$ are each independently hydrogen, —$R^{13}$—O$R^{10}$— C(=O)$R^{10}$, or —$R^{13}$—O$R^{10}$; $R^2$ and $R^8$, together with the nitrogen to which they are attached, form an optionally substituted optionally substituted heteroaryl, or optionally substituted heterocyclyl; each $R^{10}$ is independently a hydrogen, alkyl, haloalkyl and each $R^{13}$ is independently a direct bond or a straight or branched alkylene chain.

In embodiments, the compounds of Formula (Ia) are those wherein r is 0; q is 0 to 2; $R^{1a}$$R^{1b}$, $R^{1c}$, $R^{1d}$ and $R^{1e}$ are each independently hydrogen, optionally substituted aryl, optionally substituted aralkyl, optionally substituted heteroaryl; $R^3$ is a direct bond, —O—, —R$^{12}$—O—, —O—R$^{12}$—, or a straight or branched alkylene chain; R$^{4a}$ is a direct bond, or —O—; R$^{5a}$ and R$^{6a}$ are each independently hydrogen; R$^{5b}$ and R$^{6b}$ are each independently hydrogen, —R$^{13}$—OR$^{101}$—C(=O)R$^{10}$, or —R$^{13}$—OR$^{10}$; R$^2$ and R$^8$, together with the nitrogen to which they are attached, form an optionally substituted optionally substituted heteroaryl, or optionally substituted heterocyclyl; each R$^{10}$ is independently a hydrogen, alkyl, haloalkyl and each R$^{13}$ is independently a direct bond or a straight or branched alkylene chain.

In embodiments, the compounds of Formula (Ia) are those wherein r is 0; q is 2; R$^{1a}$, R$^{1b}$, R$^{1c}$, R$^{1d}$ and R$^{1e}$ are each hydrogen; R$^3$ is a straight or branched alkylene chain; R$^{4a}$ is —O—; R$^{5a}$ and R$^{6a}$ are each hydrogen; R$^{5b}$ and R$^{6b}$ are each hydrogen; R$^2$ is an alkyl and R$^8$ is an optionally substituted aralkyl. In embodiments, the aralkyl of R$^8$ is substituted with —R$^{13}$—O—R$^{10}$. In embodiments, the aralkyl of R$^8$ is substituted with —R$^{13}$—O—R$^{10}$ wherein R$^{10}$ is an optionally substituted aryl, such as an aryl-COOH.

In embodiments, some specific non-limiting compounds of Formula (I) are provided in Table I below:

TABLE I

| Chemical Formula | Hydrolase IC50 (nM) | Peptidase IC50 (nM) | Human Whole Blood IC50 (nM) |
|---|---|---|---|
| | 300 | | |
| | 41 | | 47 |
| | 44 | | 89 |
| | 100 | 32 | 370 |
| | 270 | | 150 |
| | 21 | | 310 |
| | 84 | | 880 |

TABLE I-continued

| Chemical Formula | Hydrolase IC50 (nM) | Peptidase IC50 (nM) | Human Whole Blood IC50 (nM) |
|---|---|---|---|
| (structure) | 120 | | 790 |
| (structure) | 130 | | 350 |
| (structure) | 260 | | 910 |
| (structure) | 300 | 180 | |
| (structure) | 15 | 23 | 150 |

While the compounds of the present disclosure are described with reference to specific embodiments, it should be understood by those skilled in the art that various changes may be made and equivalents may be substituted without departing from the true spirit and scope of the present disclosure.

Preparation of Compounds Described Herein

The following Reaction Schemes illustrate methods to make the compounds of Formula (I):

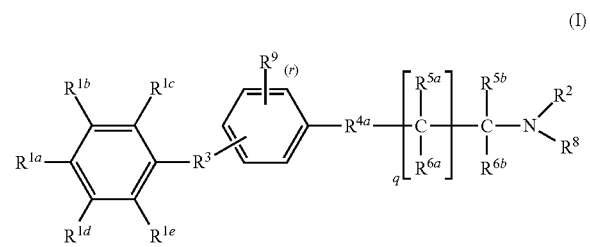

where r, q, $R^{1a}$, $R^{1b}$, $R^{1c}$, $R^{1d}$, $R^{1e}$, $R^2$, $R^3$, $R^{4a}$, $R^{5a}$, $R^{5b}$, $R^{6a}$, $R^{6b}$, $R^8$, and $R^9$ are as described above in the Summary, as single stereoisomers or as mixtures of stereoisomers, and the pharmaceutically acceptable salts, solvates, clathrates, polymorphs, ammonium ions, N-oxides or prodrugs thereof. It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(=O)—R″ (where R″ is alkyl, aryl or arylalkyl), p-methoxybenzyl, trityl and the like. Suitable protecting groups for carboxylic acid include alkyl, aryl or arylalkyl esters.

Protecting groups (PG) may be added or removed in accordance with standard techniques, which may be known to one skilled in the art and as described herein It will also be appreciated by those skilled in the art, although such protected derivatives of compounds of this disclosure may not possess pharmacological activity as such, they may be administered to a mammal and thereafter metabolized in the body to form compounds of the present disclosure which are pharmacologically active. Such derivatives may therefore be described as "prodrugs". All prodrugs of compounds described herein are included within the scope of the disclosure.

It is understood that one of ordinary skill in the art would be able to make the compounds described herein by methods similar to the methods described herein or by methods known to one of ordinary skill in the art. It is also understood that one of ordinary skill in the art would be able to make in a similar manner as described below other compounds of formula (I) not specifically illustrated below by using the appropriate starting components and modifying the parameters of the synthesis as needed. In general, compounds employed as initial starting materials in the synthesis of the compounds described herein are well known and commercially available, e.g., from Sigma Aldrich, Lancaster Synthesis, Inc., Maybridge, Matrix Scientific, TCI, and Fluorochem USA, etc. To the extent that the compounds employed as initial starting materials are not commercially available, the compounds may be readily synthesized using specific references provided, or by standard procedures commonly employed by those of ordinary skill in the art and/or found in general references text (see, for example, *Comprehensive Organic Transformations*, VCH Publishers Inc., 1989; *Compendium of Organic Synthetic Methods*, Volumes 1-10, 1974-2002, Wiley Interscience; *Advanced Organic Chemistry: Reactions, Mechanisms, and Structure*, 5th edition, Wiley Interscience, 2001; *Advanced Organic Chemistry*, 4th Edition, Part B, Reactions and Synthesis, Kluwer Academic/Plenum Publishers, 2000, etc., and references cited therein).

In the following Reaction Scheme and examples, the following common abbreviations are used:

AcOH for acetic acid
Boc for t-butoxycarbonyl
$B_2H_6$ for diborane
$CH_2O$ for formaldehyde
$ClCH_2CH_2Cl$ for 1,2-dichloroethane
DMF for N,N-dimethylformamide
$Et_2O$ for diethyl ether
EtOH for ethanol
$H_2$ for hydrogen gas
$(iPr)_2NEt$ for Hunig's Base
$K_2CO_3$ for potassium carbonate
MeCN (or $H_3C$—CN) for acetonitrile
MeOH for methanol
MsCl mesyl chloride
NaOH for sodium hydroxide
$NaBh(OAc)_3$ for sodium triacetoxyborohydride
$NaBCNH_3$ for sodium cyanoborohydride
$PH-NEt_2$ for diethyl aniline
Ra—Ni for Raney Nickel
THF for tetrahydrofuran
$Ti(O-iPr)_4$ for titanium tetraisopropoxide
TFA for trifluoroacetic acid.

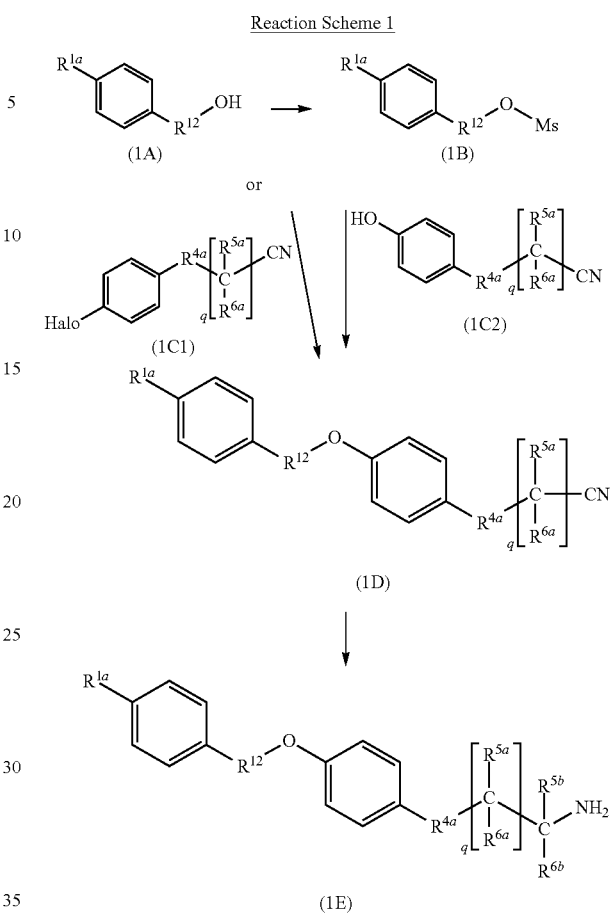

Reaction Scheme 1

Compounds (1A) and/or (1B) are commercially available and/or can be prepared by methods known to one of ordinary skill in the art. In compounds of (1A)-(1E), although only $R^{1a}$ is illustrated, $R^{1a}$ is intended to be merely representative of any of $R^{1b}$, $R^{1c}$, $R^{1d}$, and $R^{1e}$, alone or in any combination. For example, compounds (1A)-(1E) may include only $R^{1a}$ and/or compounds (1A)-(1E) may include any combination and $R^{1a}$, $R^{1b}$, $R^{1c}$, $R^{1d}$, and $R^{1e}$. Substituents q, $R^{1a}$, $R^{1b}$, $R^{1c}$, $R^{1d}$, $R^{1e}$, $R^{12}$, $R^{4a}$, $R^{5a}$, $R^{5b}$, $R^{6a}$, and $R^{6b}$ are as described in the Summary herein.

In compounds of (1C1), the halo is often Fluorine (F), but can be others as described herein. Compound (1A) can be mixed with Mesyl Chloride and pyridine to produce Compound (1B) which is includes with a pendant -Mesyl group (Ms). In embodiments, $R^{1a}$ is an optionally substituted aryl or aralkyl group and $R^{12}$ is a direct bond or alkylene chain.

Compounds (1B) and (1C2) can be mixed with diborane at 0° C. to produce compound (1D) which removes the pendant -Mesyl group and provides a pendant —CN (cyano) group. In embodiments, $R^{4a}$ is a direct bond, q is 0 to 2, and each $R^{5a}$ and $R^{6a}$ is hydrogen.

In embodiments, Compounds (1A) and (1C1) are mixed with DMF and potassium carbonate to produce Compounds (1D).

Compounds (1D) may be mixed with Raney's Nickel, hydrogen gas, and ethanol to covert the pendant —CN group to a pendant amine of Compound (1E), which is a compound according to Formula (I).

Reaction Scheme 2

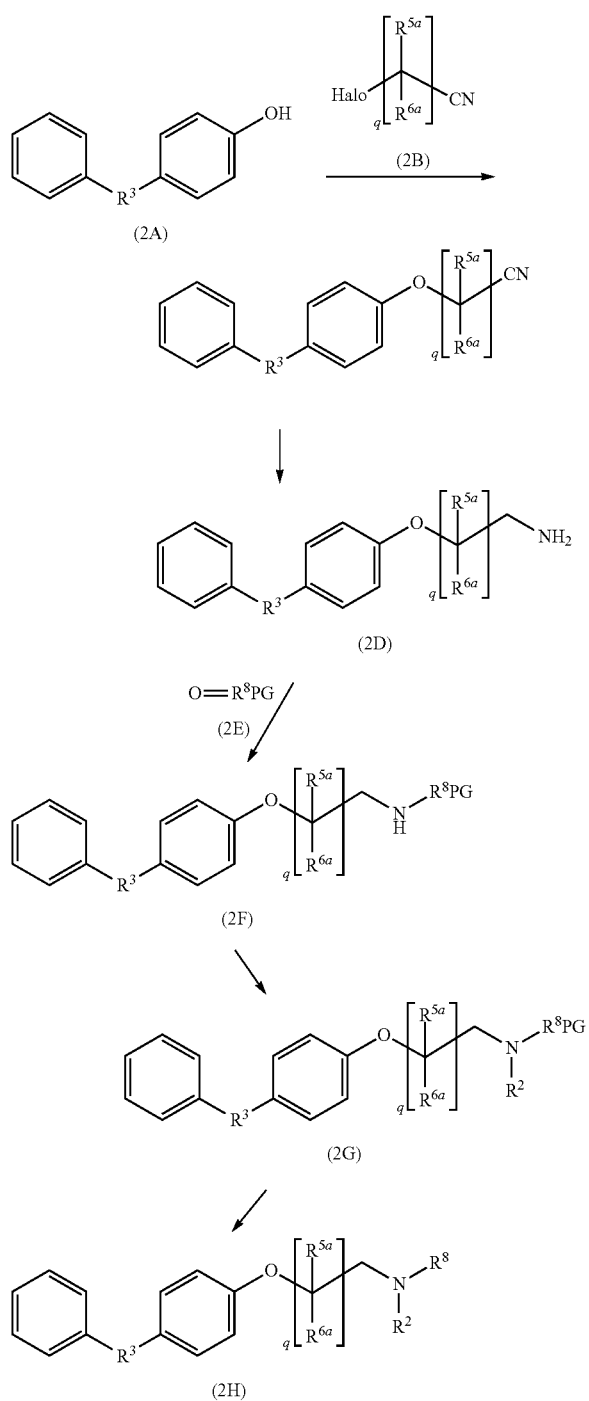

with compound (2E) and sodium triacetoxyborohydride to produce compound (2F). Compound (2F) may be mixed with formaldehyde, acetic acid, dichloroethane and sodium cyanoborohydride to produce compounds (2G).

In compounds (2E), (2F), and (2G), $R^8PG$ represents $R^8$ as described herein in a derivative form so at to be combined with a particular protective group (PG). Upon removal of the protective group (PG), $R^8PG$ becomes $R^8$ as described herein. For example, $R^8$ may be described herein as an aralkyl substituted with —COOH and in such an example, $R^8PG$ may represent an aralkyl substituted with —COO-methyl, wherein -methyl is a PG. Thus, upon removal of the PG, in this example, -methyl, $R^8PG$ returns to an aralkyl substituted with —COOH ($R^8$). Compounds (2G) and (2H) depict this process, wherein compound (2G) may be combined with sodium hydroxide and methanol to remove PG and produce compound (2H), under the proper conditions, which is a compound of Formula (I).

In embodiments, $R^3$ is an alkylene, q is 0-1, $R^{5a}$ and $R^{6a}$ are hydrogen, $R^2$ is an alkyl, and $R^8$ is an optionally substituted aryl or aralkyl.

Reaction Scheme 3

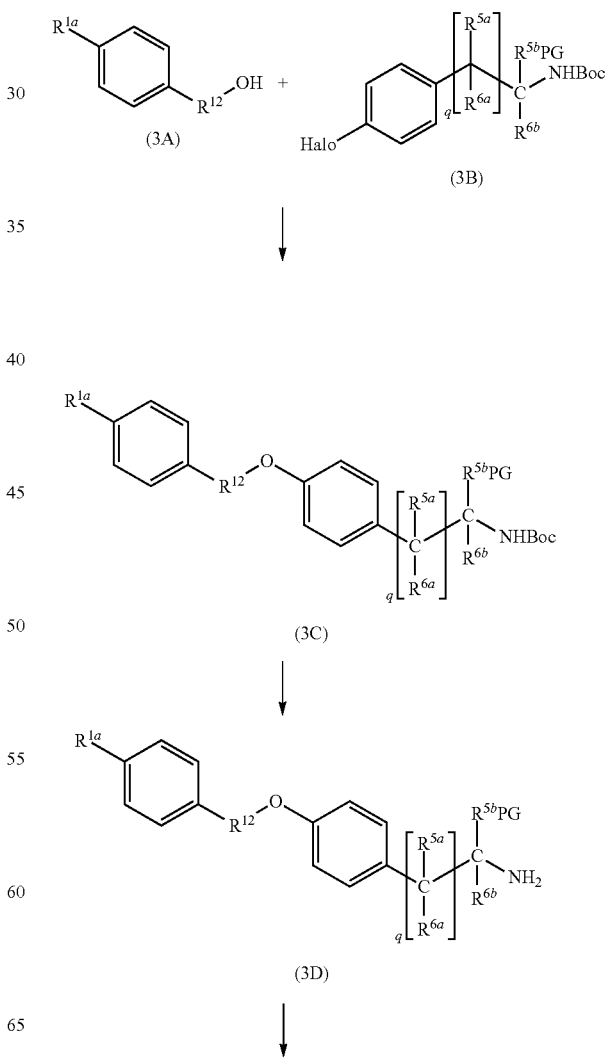

Compounds (2A) and/or (2B) are commercially available and/or can be prepared by methods known to one of ordinary skill in the art. In compounds of (2A)-(2H), each $R^3$, $R^{5a}$, $R^{6a}R^2$, and $R^8$, is as described in the Summary herein. In compounds of (2B), the halo is often Chlorine (Cl), but can be others as described herein. Compounds (2A) and (2B) can be mixed with DMF and potassium carbonate to produce compound (2C).

Compound (2C) may be mixed with THF and diborane to produce compound (2D). Compound (2D) may be combined -continued

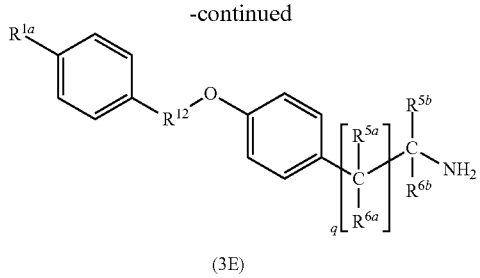

(3E)

-continued

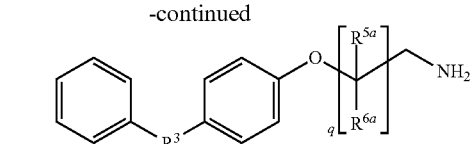

(4D)

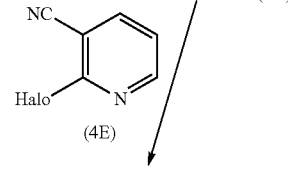

(4E)

Compounds (3A) and/or (3B) are commercially available and/or can be prepared by methods known to one of ordinary skill in the art. In compounds of (3A)-(3E), although only $R^{1a}$ is illustrated, $R^{1a}$ is intended to be merely representative of any of $R^{1b}$, $R^{1c}$, $R^{1d}$, and $R^{1e}$, alone or in any combination. For example, compounds (3A)-(3E) may include only $R^{1a}$ and/or compounds (3A)-(3E) may include any combination and $R^{1a}$, $R^{1b}$, $R^{1c}$, $R^{1d}$, and $R^{1e}$.

Substituents q, $R^{1a}$, $R^{1b}$, $R^{1c}$, $R^{1d}$, $R^{1e}$, $R^{12}$, $R^{5a}$, $R^{5b}$, $R^{6a}$, and $R^{6b}$ is as described in the Summary herein. In compound (3B), the halo is often Fluorine (F), but can be others as described herein. In Compound (3B), pendant $R^{5b}$ is combined with a protective group (PG), such as a methyl group, and the pendant NH— group is combined with a -Boc group.

Compounds (3A) and (3B) can be mixed with DMF and potassium carbonate to produce compound (3C). Compound (3C) can be mixed with TFA and dichloromethane to produce compound (3D), which in turn can be mixed with sodium hydroxide and methanol to produce compounds (3E) which follows Formula (I), and which have shed both the PG and -Boc groups.

In compounds (3B), (3C), and (3D), $R^{5b}$PG represents $R^{5b}$ as described herein in a derivative form so at to be combined with a particular protective group (PG). Upon removal of the protective group (PG), $R^{5b}$PG becomes $R^{5b}$ as described herein. Compounds (3D) and (3E) depict this process.

In embodiments, each $R^{1a}$, $R^{1b}$, $R^{1c}$, $R^{1d}$, and $R^{1e}$ is hydrogen, optionally substituted aryl, or optionally substituted aralkyl, $R^{12}$ is a direct bond; $R^{5a}$ and $R^{6a}$ are each hydrogen, q is 1; $R^{5b}$ is $R^{13}$—C(=O)OR$^{10}$ or $R^{13}$—C(OH)R$^{10}$; and $R^{5b}$ is hydrogen.

Reaction Scheme 4

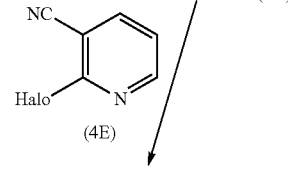

Compounds (4A) and/or (4B) are commercially available and/or can be prepared by methods known to one of ordinary skill in the art. In compounds of (4A)-(4G), each $R^3$, $R^{5a}$, $R^{6a}$ is as described in the Summary herein. In compounds of (4B) and (4E), the halo is often Chlorine (Cl), but can be others as described herein. Compound (4A) can be mixed with potassium carbonate, DMF, and compound (4B) to produce compound (4C). Compound (4C) may be mixed with THF and diborane to produce compound (4D). Compound (4D) can be mixed with potassium carbonate, DMF, and compounds (4E) to produce compound (4F). Compound (4F) may be mixed with Raney's Nickel, hydrogen gas, and ethanol to covert the pendant cyano group to a pendant amine of compounds (4G) which follow Formula (I).

In embodiments, $R^3$ is an alkylene chain or an —O—. In embodiments, $R^{5a}$ and $R^{6a}$ are hydrogen.

It is understood that other compounds described herein and not specifically disclosed in the above Reaction Schemes may be similarly prepared with the appropriate starting materials.

All compounds of the present disclosure as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of the present disclosure are intended to be within the scope of the present disclosure. Furthermore, all compounds of the present disclosure which contain an ester group can be converted to the corresponding acid by methods known to one skilled in the art or by methods described herein.

To prepare the cyclodextrin clathrates described herein, the compounds of formula (I), as defined above in the Summary, can be dissolved in a pharmacologically acceptable solvent, e.g., in an alcohol, preferably ethanol, in a ketone, e.g., acetone or in an ether, e.g., diethyl ether, and mixed with aqueous solutions of α-cyclodextrin, β-cyclodextrin or γ-cyclodextrin, preferably β-cyclodextrin, at 20° C. to 80° C.; or the acids of the compounds of formula (I) as defined above in the Summary in the form of the aqueous solutions of their salts (e.g., sodium or potassium salts) can be admixed with a cyclodextrin and after solution with the equivalent amount of an acid (e.g., HCl or $H_2SO_4$) to afford the corresponding cyclodextrin clathrate.

At this point or after cooling, the corresponding cyclodextrin clathrates separate in the form of crystals. However, it is also possible to convert oily and also crystalline compounds of formula (I), as defined above in the Summary, by rather long stirring (e.g., for 1 hour to 14 days) at ambient temperature, by treatment with an aqueous solution of cyclodextrins, into the corresponding cyclodextrin clathrate form. The clathrates can then be isolated as solid, free-flowing crystals by suctioning off the solvents and drying.

By selection of the suitable amounts of cyclodextrins and water it is possible to obtain the new clathrates in a stoichiometric composition with a reproducible content of effective substance. The clathrates can be used in a dry hygroscopic form or in a water-containing, but less hygroscopic form. A typical molar ratio of cyclodextrin to a compound of formula (I) is 2:1 (cyclodextrin:compound).

The following examples illustrate methods to make compounds of formula (I).

EXAMPLES

The following examples illustrate methods to make compounds of formula (I):

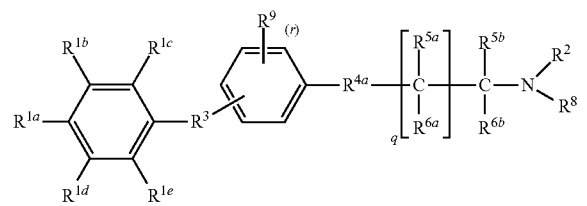

where r, q, $R^{1a}$, $R^{1b}$, $R^{1c}$, $R^{1d}$, $R^{1e}$, $R^2$, $R^3$, $R^{4a}$, $R^{5a}$, $R^{5b}$, $R^{6a}$, $R^{6b}$, $R^8$, and $R^9$ are described above in the Summary, as single stereoisomers or as mixtures of stereoisomers, and the pharmaceutically acceptable salts, solvates, clathrates, polymorphs, ammonium ions, N-oxides or prodrugs thereof. It is understood that in the following description, combinations of substituents and/or variables of the depicted formulae are permissible only if such contributions result in stable compounds.

Example 1

Preparation of Compound 1

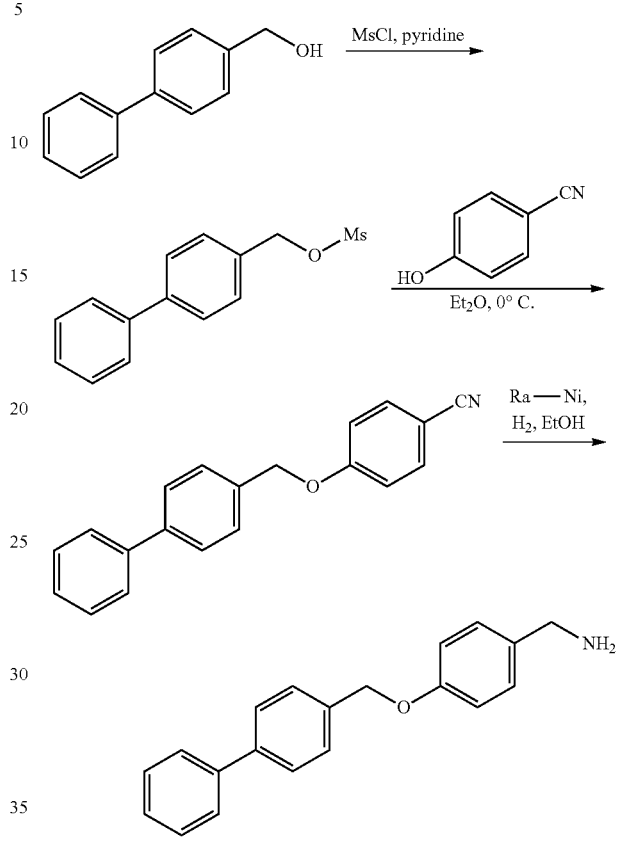

Preparation of (4-phenylphenyl)methyl methanesulfonate

To a stirred solution of 4-phenylphenylmethanol (1 eq) in pyridine was added a mesyl chloride (1 eq). The reaction mixture was stirred until no starting alcohol remained. The reaction was diluted with water and ethyl acetate. The organic phase was washed with 1N HCl, saturated aqueous copper sulfate, water and brine solution, dried over sodium sulfate and concentrated to produce (4-phenylphenyl)methyl methanesulfonate.

Preparation of 4-(4-phenylphenyl-1-methoxy)benzonitrile

To a stirred solution of (4-phenylphenyl)methyl methanesulfonate (1 eq) and potassium carbonate (1 eq) in THF was added a solution of 4-hydroxybenzonitrile (1 eq) in THF. The reaction was stirred until no starting mesylate remained. The reaction was diluted with water and extracted with diethyl ether. The combined organic extracts were washed with brine, dried and concentrated to produce 4-(4-phenylphenyl-1-methoxy)benzonitrile.

Preparation of 1-(4-phenylphenyl-1-methoxy)-4-aminomethylbenzene

To a stirred solution of 4-(4-phenylphenyl-1-methoxy) benzonitrile (1 eq) in ethanol was degassed by bubbling nitrogen into the solution and treated with Raney nickel. The reaction was placed on a Parr shaker and treated with hydrogen gas. The reaction was monitored using the hydrogen gas pressure and after uptake had stopped, the atmosphere was converted to nitrogen gas using a vacuum— nitrogen addition cycle. The mixture was filtered and the filtrate was washed with ethanol. The combined filtrates were concentrated to produce 1-(4-phenylphenyl-1-methoxy)-4-aminomethylbenzene.

The compound of Example 1 demonstrated the ability to inhibit $LTA_4$ hydrolase activity at an $IC_{50}$ value of 300 nM.

Example 2

Preparation of Compound 2

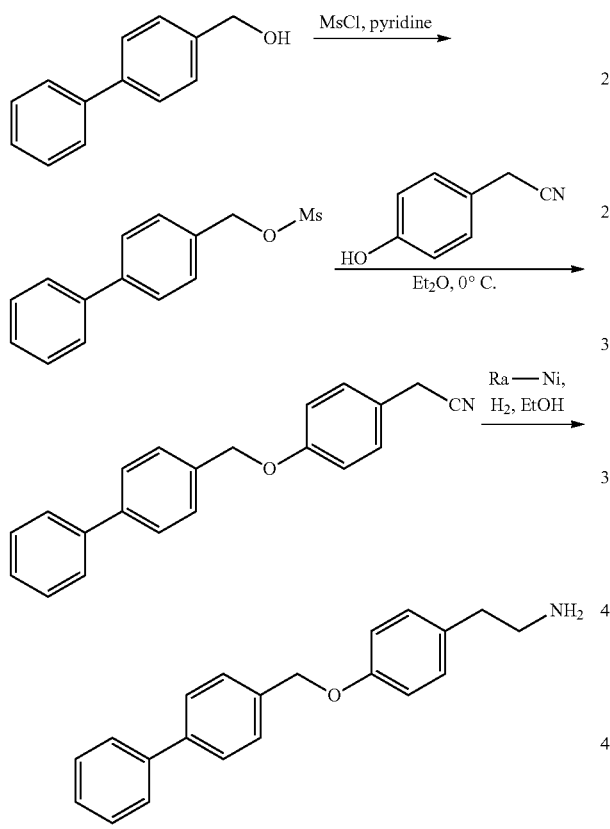

Preparation of (4-phenylphenyl)methyl methanesulfonate

To a stirred solution of 4-phenylphenylmethanol (1 eq) in pyridine was added a mesyl chloride (1 eq). The reaction mixture was stirred until no starting alcohol remained. The reaction was diluted with water and ethyl acetate. The organic phase was washed with 1N HCl, saturated aqueous copper sulfate, water and brine solution, dried over sodium sulfate and concentrated to produce (4-phenylphenyl)methyl methanesulfonate.

Preparation of 4-(4-phenylphenyl-1-methoxy)-benzylcyanide

To a stirred solution of (4-phenylphenyl)methyl methanesulfonate (1 eq) and potassium carbonate (1 eq) in THF was added a solution of 4-hydroxybenzylcyanide (1 eq) in THF. The reaction was stirred until no starting mesylate remained. The reaction was diluted with water and extracted with diethyl ether. The combined organic extracts were washed with brine, dried and concentrated to produce 4-(4-phenylphenyl-1-methoxy)-benzylcyanide.

Preparation of (4-phenylphenyl-1-methoxy)-4-phenylethylamine

To a stirred solution of 4-(4-phenylphenyl-1-methoxy) benzylcyanide (1 eq) in ethanol was degassed by bubbling nitrogen into the solution and treated with Raney nickel. The reaction was placed on a Parr shaker and treated with hydrogen gas. The reaction was monitored using the hydrogen gas pressure and after uptake had stopped, the atmosphere was converted to nitrogen gas using a vacuum— nitrogen addition cycle. The mixture was filtered and the filtrate was washed with ethanol. The combined filtrates were concentrated to produce (4-phenylphenyl-1-methoxy)-4-phenylethylamine.

The compound of Example 2 demonstrated the ability to inhibit: $LTA_4$ hydrolase activity at an $IC_{50}$ value of 41 nM; and the production of $LTB_4$ in whole blood at an $IC_{50}$ value of 47 nM.

Example 3

Preparation of Compound 3

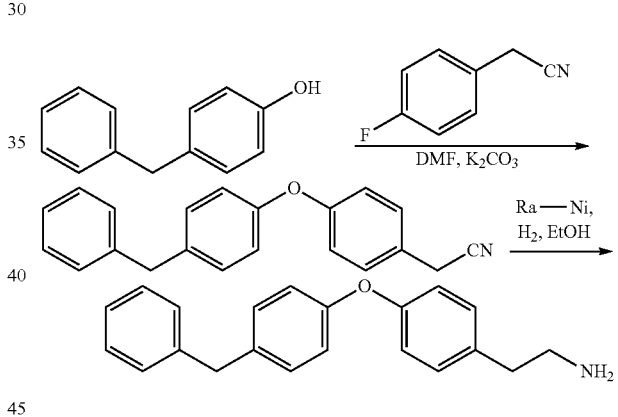

Preparation of (4-benzylphenoxy)benzylcyanide

To a stirred solution of 4-benzylphenol (1 eq) and potassium carbonate (1.1 eq) in DMF was added 4-fluorobenzylcyanide (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce (4-benzylphenoxy)benzylcyanide.

Preparation of 4-benzylphenoxy-4-phenylethylamine

To a stirred solution of (4-benzylphenoxy)benzylcyanide (1 eq) in ethanol was degassed by bubbling nitrogen into the solution and treated with Raney nickel. The reaction was placed on a Parr shaker and treated with hydrogen gas. The reaction was monitored using the hydrogen gas pressure and after uptake had stopped, the atmosphere was converted to nitrogen gas using a vacuum—nitrogen addition cycle. The mixture was filtered and the filtrate was washed with ethanol. The combined filtrates were concentrated to produce 4-benzylphenoxy-4-phenylethylamine.
The compound of Example 3 demonstrated the ability to inhibit: LTA$_4$ hydrolase activity at an IC$_{50}$ value of 44 nM; and the production of LTB$_4$ in whole blood at an IC$_{50}$ value of 89 nM.
Example 4
Preparation of Compound 4
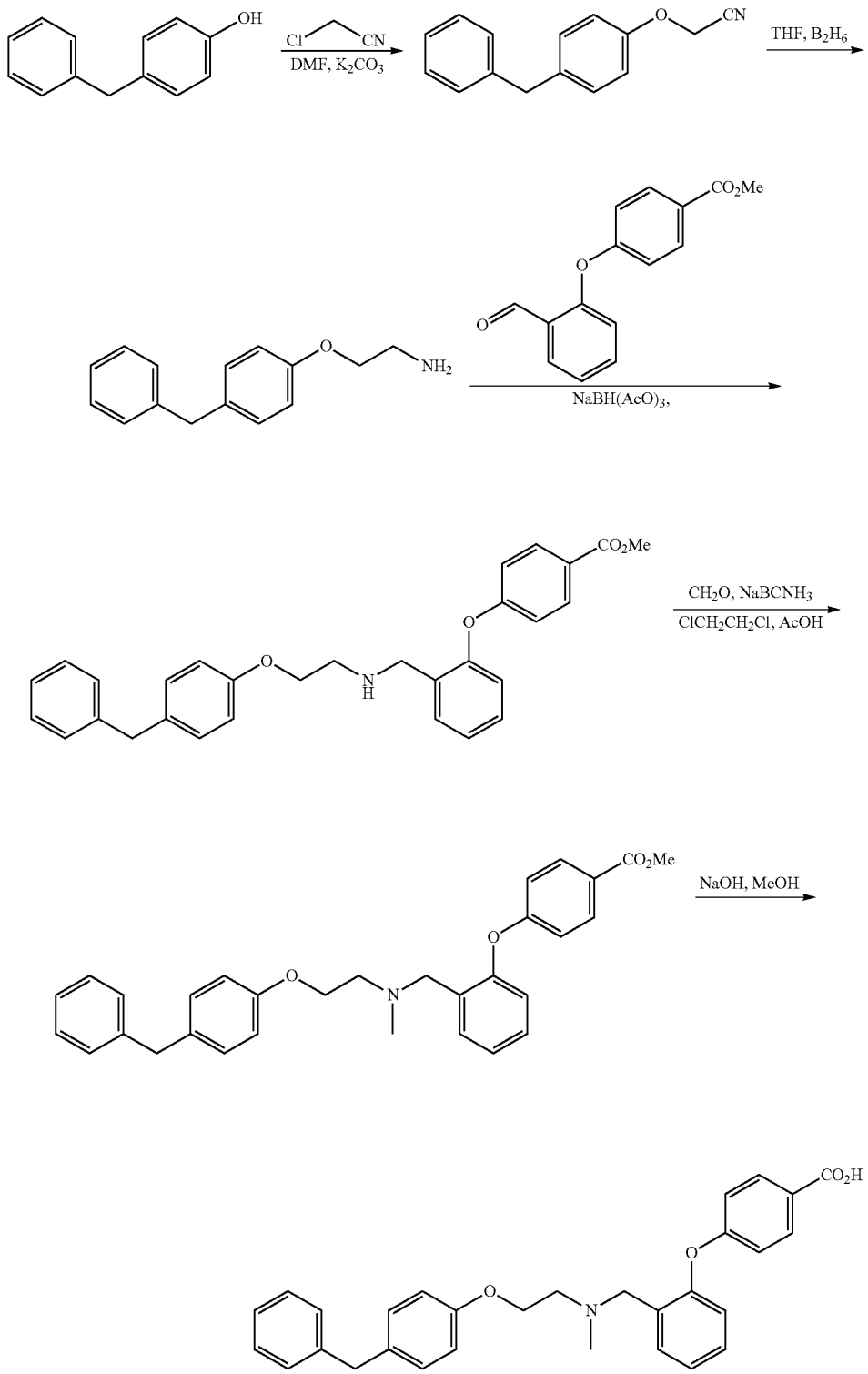

Preparation of (4-benzylphenoxy)acetonitrile

To a stirred solution of 4-benzylphenol (1 eq) and potassium carbonate (1.1 eq) in DMF was added chloroacetonitrile (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce (4-benzylphenoxy)acetonitrile.

Preparation of 2-(4-benzylphenoxy)ethylamine

To a stirred solution of (4-benzylphenoxy)acetonitrile (1 eq) in THF was added a solution of diborane in THF (1M, 1.1 eq). The reaction was stirred until no starting material remained. The reaction was diluted with water and extracted with ethyl acetate. The combined organic extracts were washed with brine, dried and concentrated to produce 2-(4-benzylphenoxy)ethylamine.

Preparation of methyl [N-2-(4-benzylphenoxy)ethyl](2-aminomethylphenoxy)-4-benzoate To a stirred solution of methyl 4-(2-formylphenoxy)benzoate (1 eq) and 2-(4-benzylphenoxy)ethylamine (1 eq) in dichloroethane was added a triacetoxyborohydride (2 eq). The reaction was stirred until no starting amine remained. The reaction was diluted with water and extracted with ethyl acetate. The combined organic extracts were washed with brine, dried and concentrated to produce methyl [N-2-(4-benzylphenoxy)ethyl](2-aminomethylphenoxy)-4-benzoate.

Preparation of methyl [N-2-(4-benzylphenoxy)ethyl]-N-methyl-(2-aminomethylphenoxy)-4-benzoate To a stirred solution of methyl [N-2-(4-benzylphenoxy)ethyl](2-aminomethylphenoxy)-4-benzoate (1 eq) and aqueous formaldehyde (1.1 eq) in acetonitrile and acetic acid was added a solution of sodium cyanoborohydride (2 eq) in acetonitrile. The reaction was stirred until no starting secondary amine remained. The reaction was diluted with water and extracted with ethyl acetate. The combined organic extracts were washed with brine, dried and concentrated to produce methyl [N-2-(4-benzylphenoxy)ethyl]-N-methyl-(2-aminomethylphenoxy)-4-benzoate.

Preparation of [N-2-(4-benzylphenoxy)ethyl]-N-methyl-(2-aminomethylphenoxy)-4-benzoic acid To a stirred solution of sodium hydroxide (1.1 eq) in methanol was added methyl [N-2-(4-benzylphenoxy)ethyl]-N-methyl-(2-aminomethylphenoxy)-4-benzoate (1 eq). The reaction was stirred until no starting ester remained. The reaction was diluted with water and extracted with ethyl acetate. The combined organic extracts were washed with brine, dried and concentrated.

The compound of Example 4 demonstrated the ability to inhibit: $LTA_4$ hydrolase activity at an $IC_{50}$ value of 100 nM; peptidase activity at an $IC_{50}$ value of 32 nM; and the production of $LTB_4$ in whole blood at an $IC_{50}$ value of 370 nM.

Example 5

Preparation of Compound 5

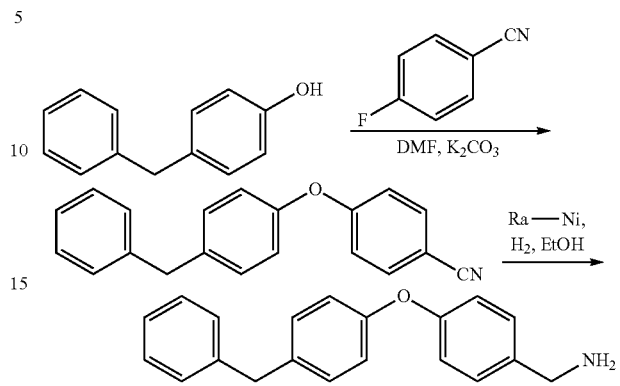

Preparation of 4-(4-benzylphenoxy)benzonitrile

To a stirred solution of 4-benzylphenol (1 eq) and potassium carbonate (1.1 eq) in DMF was added 4-fluorobenzonitrile (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce 4-(4-benzylphenoxy)benzonitrile.

Preparation of 4-(4-benzylphenoxy)benzylamine

To a stirred solution of 4-(4-benzylphenoxy)benzonitrile (1 eq) in ethanol was degassed by bubbling nitrogen into the solution and treated with Raney nickel. The reaction was placed on a Parr shaker and treated with hydrogen gas. The reaction was monitored using the hydrogen gas pressure and after uptake had stopped, the atmosphere was converted to nitrogen gas using a vacuum—nitrogen addition cycle. The mixture was filtered and the filtrate was washed with ethanol. The combined filtrates were concentrated to produce 4-(4-benzylphenoxy)benzylamine.

The compound of Example 5 demonstrated the ability to inhibit: $LTA_4$ hydrolase activity at an $IC_{50}$ value of 270 nM; and the production of $LTB_4$ in whole blood at an $IC_{50}$ value of 150 nM.

Example 6

Preparation of Compound 6

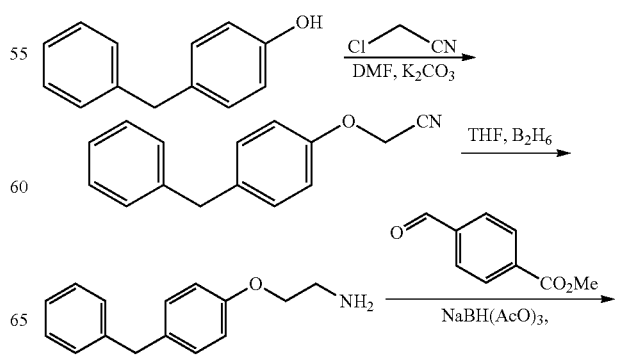

-continued

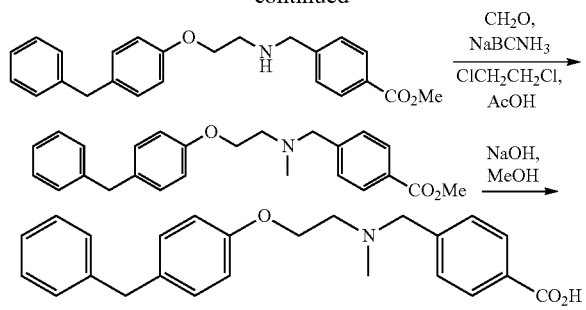

Preparation of (4-benzylphenoxy)acetonitrile

To a stirred solution of 4-benzylphenol (1 eq) and potassium carbonate (1.1 eq) in DMF was added chloroacetonitrile (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce (4-benzylphenoxy)acetonitrile.

Preparation of 2-(4-benzylphenoxy)ethylamine

To a stirred solution of (4-benzylphenoxy)acetonitrile (1 eq) in THF was added a solution of diborane in THF (1M, 1.1 eq). The reaction was stirred until no starting material remained. The reaction was diluted with water and extracted with ethyl acetate. The combined organic extracts were washed with brine, dried and concentrated to produce 2-(4-benzylphenoxy)ethylamine.

Preparation of methyl [N-2-(4-benzylphenoxy)ethyl]-4-aminomethylbenzoate

To a stirred solution of methyl 4-formylbenzoate (1 eq) and 2-(4-benzylphenoxy)ethylamine (1 eq) in dichloroethane was added a triacetoxyborohydride (2 eq). The reaction was stirred until no starting amine remained. The reaction was diluted with water and extracted with ethyl acetate. The combined organic extracts were washed with brine, dried and concentrated to give named compound.

Preparation of methyl [N-2-(4-benzylphenoxy)ethyl]-N-methyl-aminomethyl-4-benzoate To a stirred solution of [N-2-(4-benzylphenoxy)ethyl]aminomethyl-4-benzoate (1 eq) and aqueous formaldehyde (1.1 eq) in acetonitrile and acetic acid was added a solution of sodium cyanoborohydride (2 eq) in acetonitrile. The reaction was stirred until no starting secondary amine remained. The reaction was diluted with water and extracted with ethyl acetate. The combined organic extracts were washed with brine, dried and concentrated to produce methyl [N-2-(4-benzylphenoxy)ethyl]-N-methyl-aminomethyl-4-benzoate.

Preparation of [N-2-(4-benzylphenoxy)ethyl]-N-methyl-aminomethyl-4-benzoic acid To a stirred solution of sodium hydroxide (1.1 eq) in methanol was added methyl [N-2-(4-benzylphenoxy)ethyl]-N-methyl-aminomethyl-4-benzoate (1 eq). The reaction was stirred until no starting ester remained. The reaction was diluted with water and extracted with ethyl acetate. The combined organic extracts were washed with brine, dried and concentrated.

The compound of Example 6 demonstrated the ability to inhibit: $LTA_4$ hydrolase activity at an $IC_{50}$ value of 21 nM; and the production of $LTB_4$ in whole blood at an $IC_{50}$ value of 310 nM.

Example 7

Preparation of Compound 7

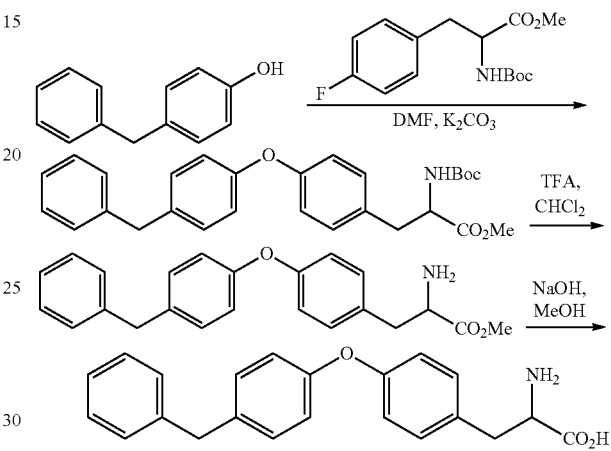

Preparation of methyl 3-[4-(4-benzylphenoxy)phenyl]-2-[(tert-butoxycarbamoyl)amino]propanoate To a stirred solution of 4-benzylphenol (1 eq) and potassium carbonate (1.1 eq) in DMF was added methyl 3-fluorophenyl-2-[(tert-butoxycarbamoyl)amino]propanoate (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce methyl 3-[4-(4-benzylphenoxy)phenyl]-2-[(tert-butoxycarbamoyl)amino]propanoate.

Preparation of methyl 3-[4-(4-benzylphenoxy)phenyl]-2-aminopropanoate

To a stirred solution of methyl 3-[4-(4-benzylphenoxy)phenyl]-2-[(tert-butoxycarbamoyl)amino]propanoate (1 eq) in dichloromethane was added trifluoroacetic acid. The reaction was stirred until no starting material remained. The reaction was diluted with water, neutralized with aqueous sodium hydroxide (1N) and extracted with ethyl acetate. The combined organic extracts were washed with brine, dried and concentrated to produce methyl 3-[4-(4-benzylphenoxy)phenyl]-2-aminopropanoate.

Preparation of 3-[4-(4-benzylphenoxy)phenyl]-2-aminopropanoic acid

To a stirred solution of sodium hydroxide (1.1 eq) in methanol was added methyl 3-[4-(4-benzylphenoxy)phenyl]-2-aminopropanoate (1 eq). The reaction was stirred until no starting ester remained. The reaction was diluted with water and extracted with ethyl acetate. The combined organic extracts were washed with brine, dried and concentrated.

The compound of Example 7 demonstrated the ability to inhibit: $LTA_4$ hydrolase activity at an $IC_{50}$ value of 84 nM; and the production of $LTB_4$ in whole blood at an $IC_{50}$ value of 880 nM.

Example 8

Preparation of Compound 8

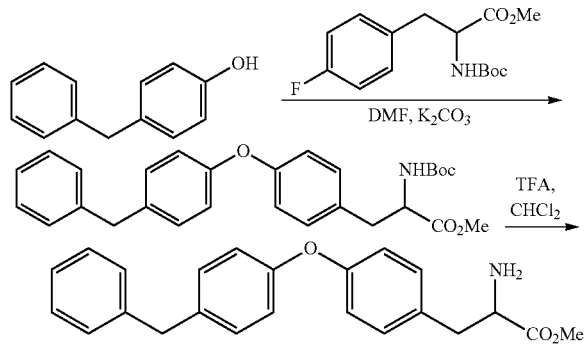

Preparation of methyl 3-[4-(4-benzylphenoxy)phenyl]-2-[(tert-butoxycarbamoyl)amino]propanoate To a stirred solution of 4-benzylphenol (1 eq) and potassium carbonate (1.1 eq) in DMF was added methyl 3-fluorophenyl-2-[(tert-butoxycarbamoyl)amino]propanoate (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce methyl 3-[4-(4-benzylphenoxy)phenyl]-2-[(tert-butoxycarbamoyl)amino]propanoate.

Preparation of methyl 3-[4-(4-benzylphenoxy)phenyl]-2-aminopropanoate

To a stirred solution of methyl 3-[4-(4-benzylphenoxy)phenyl]-2-[(tert-butoxycarbamoyl)amino]propanoate (1 eq) in dichloromethane was added trifluoroacetic acid. The reaction was stirred until no starting material remained. The reaction was diluted with water, neutralized with aqueous sodium hydroxide (1N) and extracted with ethyl acetate. The combined organic extracts were washed with brine, dried and concentrated to produce methyl 3-[4-(4-benzylphenoxy)phenyl]-2-aminopropanoate.

The compound of Example 8 demonstrated the ability to inhibit: $LTA_4$ hydrolase activity at an $IC_{50}$ value of 120 nM; and the production of $LTB_4$ in whole blood at an $IC_{50}$ value of 790 nM.

Example 9

Preparation of Compound 9

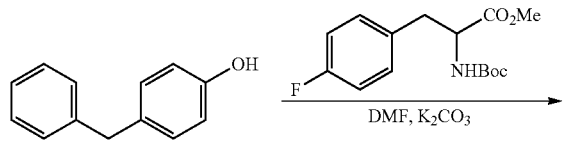

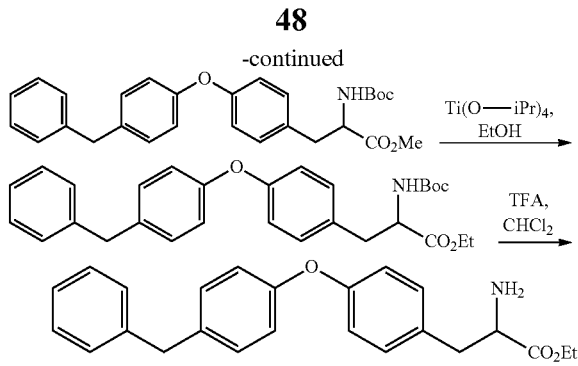

Preparation of methyl 3-[4-(4-benzylphenoxy)phenyl]-2-[(tert-butoxycarbamoyl)amino]propanoate To a stirred solution of 4-benzylphenol (1 eq) and potassium carbonate (1.1 eq) in DMF was added methyl 3-fluorophenyl-2-[(tert-butoxycarbamoyl)amino]propanoate (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce methyl 3-[4-(4-benzylphenoxy)phenyl]-2-[(tert-butoxycarbamoyl)amino]propanoate.

Preparation of ethyl 3-[4-(4-benzylphenoxy)phenyl]-2-[(tert-butoxycarbamoyl)amino]propanoate To a stirred solution of methyl 3-[4-(4-benzylphenoxy)phenyl]-2-[(tert-butoxycarbamoyl)amino]propanoate (1 eq) in ethanol was added titanium tetraisopropoxide (0.1 eq). The reaction was stirred until no starting material remained. The reaction was diluted with water and extracted with ethyl acetate. The combined organic extracts were washed with brine, dried and concentrated to produce ethyl 3-[4-(4-benzylphenoxy)phenyl]-2-[(tert-butoxycarbamoyl)amino] propanoate.

Preparation of ethyl 3-[4-(4-benzylphenoxy)phenyl]-2-aminopropanoate

To a stirred solution of methyl 3-[4-(4-benzylphenoxy)phenyl]-2-[(tert-butoxycarbamoyl)amino]propanoate (1 eq) in dichloromethane was added trifluoroacetic acid. The reaction was stirred until no starting material remained. The reaction was diluted with water, neutralized with aqueous sodium hydroxide (1N) and extracted with ethyl acetate. The combined organic extracts were washed with brine, dried and concentrated to produce ethyl 3-[4-(4-benzylphenoxy)phenyl]-2-aminopropanoate.

The compound of Example 9 demonstrated the ability to inhibit: $LTA_4$ hydrolase activity at an $IC_{50}$ value of 130 nM; and the production of $LTB_4$ in whole blood at an $IC_{50}$ value of 350 nM.

Example 10

Preparation of Compound 10

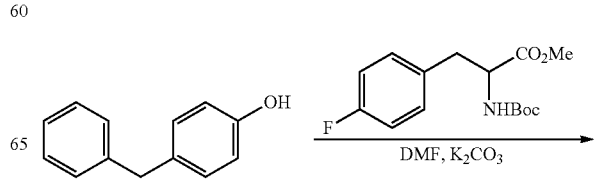

-continued

Preparation of methyl 3-[4-(4-benzylphenoxy)phenyl]-2-[(tert-butoxycarbamoyl)amino]propanoate To a stirred solution of 4-benzylphenol (1 eq) and potassium carbonate (1.1 eq) in DMF was added methyl 3-fluorophenyl-2-[(tert-butoxycarbamoyl)amino]propanoate (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce methyl 3-[4-(4-benzylphenoxy)phenyl]-2-[(tert-butoxycarbamoyl)amino]propanoate.

Preparation of 3-[4-(4-benzylphenoxy)phenyl]-2-[(tert-butoxycarbamoyl)amino]propanol To a stirred solution of methyl 3-[4-(4-benzylphenoxy)phenyl]-2-[(tert-butoxycarbamoyl)amino]propanoate (1 eq) in methanol/THF (3/1) heated at 50° C. was added Sodium borohydride (4 eq). The reaction was stirred until no starting material remained. The reaction was poured into iced aqueous HCl (0.5M). The resulting solid was isolated by filtration, washed with water, and dried to produce 3-[4-(4-benzylphenoxy)phenyl]-2-[(tert-butoxycarbamoyl)amino]propanol.

Preparation of 3-[4-(4-benzylphenoxy)phenyl]-2-aminopropanol

To a stirred solution of 3-[4-(4-benzylphenoxy)phenyl]-2-[(tert-butoxycarbamoyl)amino]propanol (1 eq) in dichloromethane was added trifluoroacetic acid. The reaction was stirred until no starting material remained. The reaction was diluted with water, neutralized with aqueous sodium hydroxide (1N) and extracted with ethyl acetate. The combined organic extracts were washed with brine, dried and concentrated to produce 3-[4-(4-benzylphenoxy)phenyl]-2-aminopropanol.

The compound of Example 10 demonstrated the ability to inhibit: $LTA_4$ hydrolase activity at an $IC_{50}$ value of 260 nM; and the production of $LTB_4$ in whole blood at an $IC_{50}$ value of 910 nM.

Example 11

Preparation of Compound 11

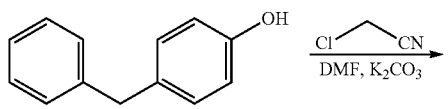

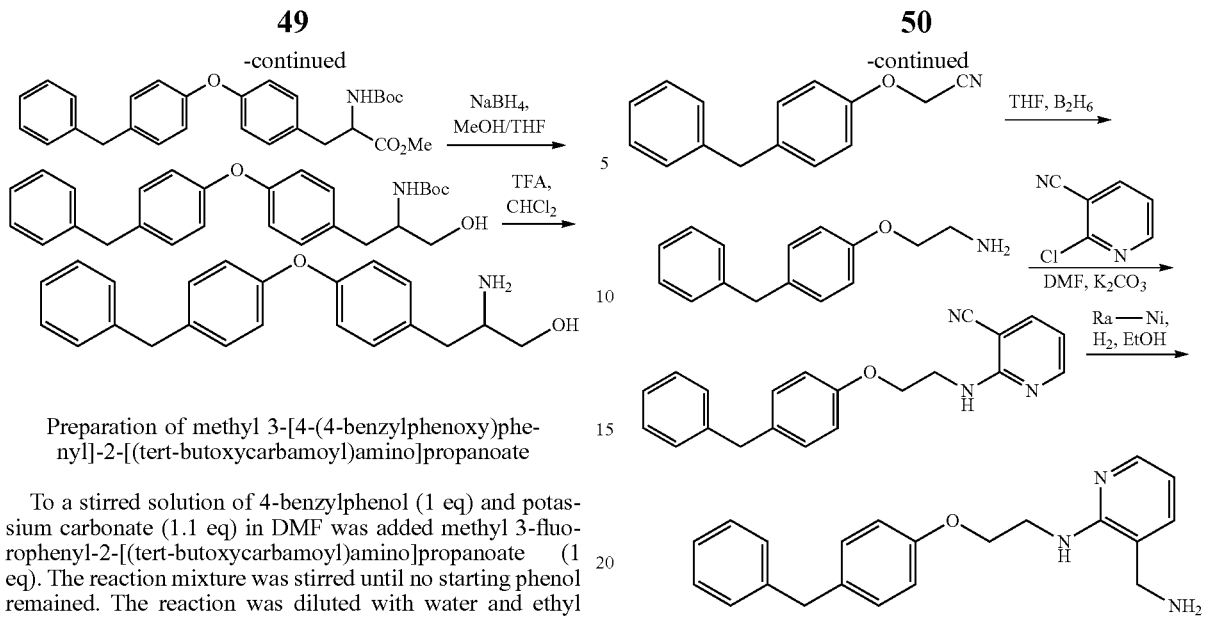

Preparation of (4-benzylphenoxy)acetonitrile

To a stirred solution of 4-benzylphenol (1 eq) and potassium carbonate (1.1 eq) in DMF was added chloroacetonitrile (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce (4-benzylphenoxy)acetonitrile.

Preparation of 2-(4-benzylphenoxy)ethylamine

To a stirred solution of (4-benzylphenoxy)acetonitrile (1 eq) in THF was added a solution of diborane in THF (1M, 1.1 eq). The reaction was stirred until no starting material remained. The reaction was diluted with water and extracted with ethyl acetate. The combined organic extracts were washed with brine, dried and concentrated to produce 2-(4-benzylphenoxy)ethylamine.

Preparation of 2-(4-benzylphenoxy)ethylamine-3-pyridinecarbonitrile

To a stirred solution of 2-(4-benzylphenoxy)ethylamine (1 eq) and potassium carbonate (1.1 eq) in DMF was added 2-chloro-pyridinecarbonitrile (1 eq). The reaction mixture was stirred until no starting phenol remained. The reaction was diluted with water and ethyl acetate. The organic phase was washed with 1N HCl, saturated aqueous copper sulfate, water and brine solution, dried over sodium sulfate and concentrated to produce 2-(4-benzylphenoxy)ethylamine-3-pyridinecarbonitrile.

Preparation of 2-(4-benzylphenoxy)ethylamino-3-aminomethylpyridine

To a stirred solution of 2-(4-benzylphenoxy)ethylamine-3-pyridinecarbonitrile (1 eq) in ethanol was degassed by bubbling nitrogen into the solution and treated with Raney nickel. The reaction was placed on a Parr shaker and treated with hydrogen gas. The reaction was monitored using the hydrogen gas pressure and after uptake had stopped, the atmosphere was converted to nitrogen gas using a vacuum—nitrogen addition cycle. The mixture was filtered and the filtrate was washed with ethanol. The combined filtrates were concentrated to produce 2-(4-benzylphenoxy)ethyl-amino-3-aminomethylpyridine.

The compound of Example 11 demonstrated the ability to inhibit: $LTA_4$ hydrolase activity at an $IC_{50}$ value of 300 nM; and peptidase activity at an $IC_{50}$ value of 180 nM.

Example 12

Preparation of Compound 12

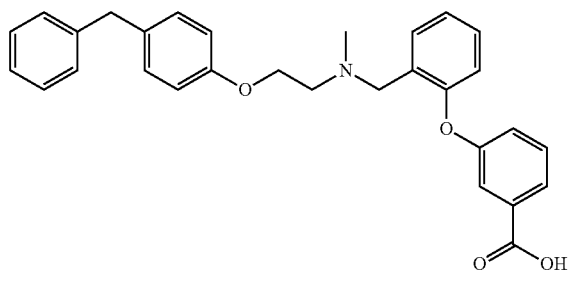 [SMILES: CN(CCOc1ccc(Cc2ccccc2)cc1)Cc1ccccc1Oc1cccc(C(=O)O)c1]

The preparation of compound 12 was performed in a manner similar to the preparation of Compound 4 in Example 4, however starting material methyl 4(2-formylphenoxy)benzoate was be substituted with methyl 3(2-formylphenoxy)benzoate. The reaction proceeded under the proper conditions as in Example 4 with the intermediate names reflecting the change in terminal benzoic acid from the para position in Example 4 to the meta position as shown in Compound 12.

The compound of Example 12 demonstrated the ability to inhibit: $LTA_4$ hydrolase activity at an $IC_{50}$ value of 15 nM; and, peptidase activity at an $IC_{50}$ value of 23 nM; and production of $LTB_4$ in whole blood at $IC_{50}$ value of 150 nM.

What is claimed is:

1. A compound having the formula (I):

(I)

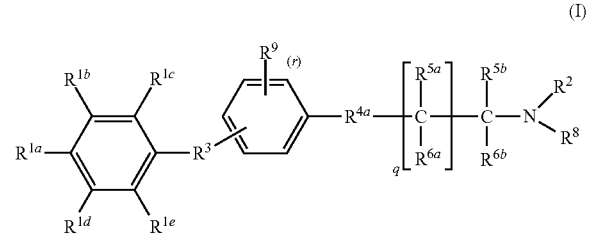

wherein:
r is 0; q is 0 to 2;
$R^{1a}, R^{1b}, R^{1c}, R^{1d}$ and $R^{1e}$ are each independently selected from the group consisting of hydrogen, $C_1$-$C_6$ alkyl, halo, optionally substituted aryl, and optionally substituted heteroaryl;

$R^2$ is hydrogen or $C_1$-$C_6$ alkyl;
$R^8$ is benzyl substituted with $R^{13}$ —O—$R^{10}$;
$R^3$ is methylene;
$R^{4a}$ is —O—;
$R^{5a}$ and $R^{6a}$ are each hydrogen;
$R^{5b}$ and $R^{6b}$ are each hydrogen;
$R^{10}$ is phenyl substituted with $C(O)OR^{15}$;
and
each $R^{13}$ is a direct bond; and
$R^{15}$ is hydrogen or $C_1$-$C_6$ alkyl;
as a single stereoisomer or as a mixture of stereoisomers; or a pharmaceutically acceptable salt.

2. The compound according to claim 1, wherein $R^{1a}$, $R^{1b}$, $R^{1c}$, $R^{1d}$ and $R^{1e}$ are each independently hydrogen; or a pharmaceutically acceptable salt thereof.

3. The compound according to claim 1 wherein $R^2$ is hydrogen; or a pharmaceutically acceptable salt thereof.

4. The compound according to claim 1, wherein the compound is selected from one of the following compounds, or is a pharmaceutically acceptable salt thereof:

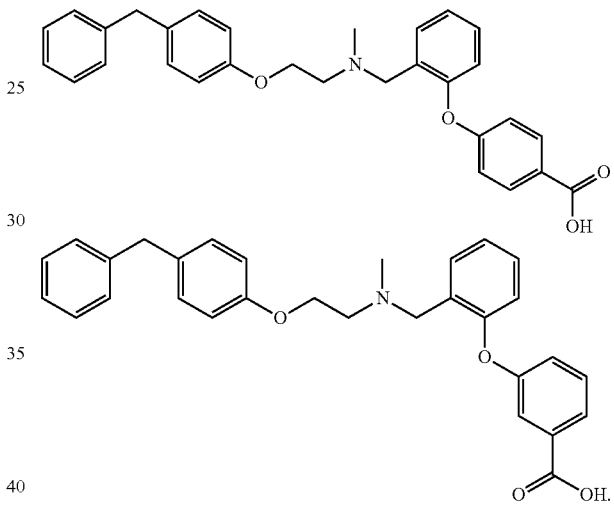

5. The compound according to claim 1, wherein q is 1, or a pharmaceutically acceptable salt thereof.

6. The compound according to claim 1, wherein $R^2$ is methyl, or a pharmaceutically acceptable salt thereof.

7. The compound according to claim 1, wherein $R^{15}$ is hydrogen, or a pharmaceutically acceptable salt thereof.

8. The compound according to claim 2, wherein q is 1, or a pharmaceutically acceptable salt thereof.

9. The compound according to claim 8, wherein $R^2$ is methyl, or a pharmaceutically acceptable salt thereof.

10. The compound according to claim 9, wherein $R^{15}$ is hydrogen, or a pharmaceutically acceptable salt thereof.

11. A pharmaceutical composition comprising a pharmaceutically acceptable excipient and a therapeutically effective amount of a compound according to claim 1, or a pharmaceutically acceptable salt thereof.

* * * * *